(12) United States Patent
Smith et al.

(10) Patent No.: US 10,545,083 B2
(45) Date of Patent: Jan. 28, 2020

(54) DROPLET SORTING BASED ON IONIZATION MASS SPECTROMETRY

(71) Applicant: Sphere Fluidics Limited, Cambridge (GB)

(72) Inventors: Clive Adrian Smith, Hertford (GB); Xin Li, Cambridge (GB); Frank F. Craig, Cambridge (GB)

(73) Assignee: Sphere Fluidics Limited, Cambridge (GB)

( * ) Notice: Subject to any disclaimer, the term of this patent is extended or adjusted under 35 U.S.C. 154(b) by 0 days.

(21) Appl. No.: 15/502,630

(22) PCT Filed: Aug. 7, 2015

(86) PCT No.: PCT/GB2015/052301
§ 371 (c)(1),
(2) Date: Feb. 8, 2017

(87) PCT Pub. No.: WO2016/024095
PCT Pub. Date: Feb. 18, 2016

(65) Prior Publication Data
US 2017/0227440 A1 Aug. 10, 2017

(30) Foreign Application Priority Data

Aug. 11, 2014 (GB) .................................. 1414177.4

(51) Int. Cl.
*G01N 15/10* (2006.01)
*B01L 3/00* (2006.01)
(Continued)

(52) U.S. Cl.
CPC ...... *G01N 15/1031* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS

| 2003/0136904 A1 | 7/2003 | Mukaibatake |
| 2004/0026617 A1 | 2/2004 | Gregori et al. |

(Continued)

FOREIGN PATENT DOCUMENTS

| WO | WO 2004/038363 A2 | 5/2004 |
| WO | WO 2007/120240 A2 | 10/2007 |
| WO | WO 2012/001421 A1 | 1/2012 |

OTHER PUBLICATIONS https://web.archive.org/web/20130318015016/https://pmm.nasa.gov/education/articles/shape-of-a-raindrop.*

(Continued)

*Primary Examiner* — James Choi
(74) *Attorney, Agent, or Firm* — Wolf, Greenfield & Sacks, P.C.

(57) ABSTRACT

We describe a method comprising: providing a droplet comprising a plurality of constituents, splitting said droplet into a first droplet and a second droplet, wherein said first droplet comprises a first fraction of said plurality of constituents and said second droplet comprises a second fraction of said plurality of constituents, analysing said constituents of said first fraction of said plurality of constituents in said first droplet, and sorting said second droplet dependent on an outcome of said analysis.

20 Claims, 11 Drawing Sheets

(51) Int. Cl.
*H01J 49/04* (2006.01)
*H01J 49/00* (2006.01)

(52) U.S. Cl.
CPC .... *B01L 3/502784* (2013.01); *G01N 15/1056* (2013.01); *B01L 2200/0652* (2013.01); *B01L 2300/0627* (2013.01); *B01L 2300/0816* (2013.01); *B01L 2300/0864* (2013.01); *B01L 2400/0424* (2013.01); *G01N 2015/1081* (2013.01); *H01J 49/0031* (2013.01); *H01J 49/04* (2013.01)

(56) References Cited

U.S. PATENT DOCUMENTS

| | | | |
|---|---|---|---|
| 2008/0014589 A1* | 1/2008 | Link | B01F 3/0807 435/287.2 |
| 2008/0166793 A1* | 7/2008 | Beer | B01L 3/502753 435/287.2 |
| 2009/0203063 A1 | 8/2009 | Wheller et al. | |
| 2010/0055677 A1 | 3/2010 | Colston et al. | |
| 2010/0213074 A1 | 8/2010 | Mousa et al. | |
| 2011/0107822 A1 | 5/2011 | Bunner et al. | |
| 2012/0153143 A1 | 6/2012 | Kennedy et al. | |
| 2012/0217389 A1 | 8/2012 | Zheng et al. | |
| 2013/0187040 A1* | 7/2013 | Abell | H01J 49/16 250/282 |

OTHER PUBLICATIONS

PCT/GB2015/052301, Oct. 28, 2015, Invitation to Pay Additional Fees.
Invitation to Pay Additional Fees for International Application No. PCT/GB2015/052301 dated Oct. 28, 2015.
[No Author Listed] FT-NMR Sample Preparation Guide. Sep. 7, 2012. pp 55-57. Retrieved from the Internet on Oct. 16, 2016 at https://ocw.mit.edu/courses/chemistry/5-301-chemistry-laboratory-techniques-january-iap-2012/labs/MIT5_301IAP12_NMR_Handout.pdf.
International Search Report and Written Opinion for International Application No. PCT/GB2015/052301 dated Jan. 12, 2016.
International Preliminary Report on Patentability for International Application No. PCT/GB2015/052301 dated Feb. 23, 2017.

* cited by examiner

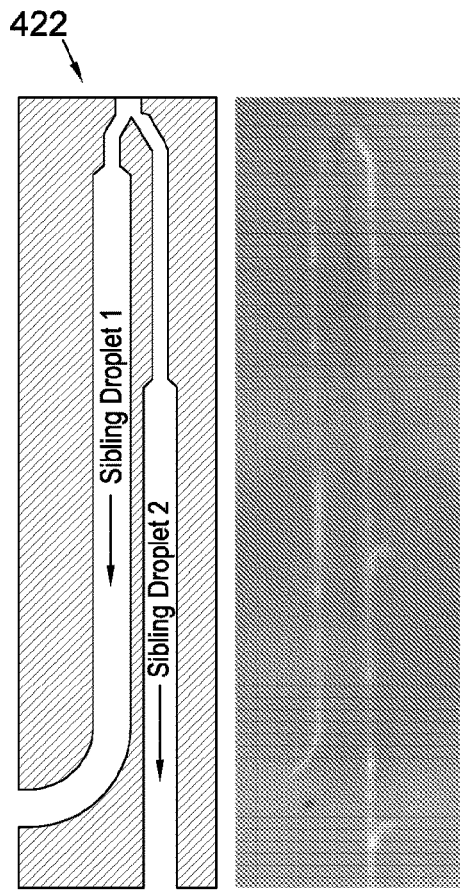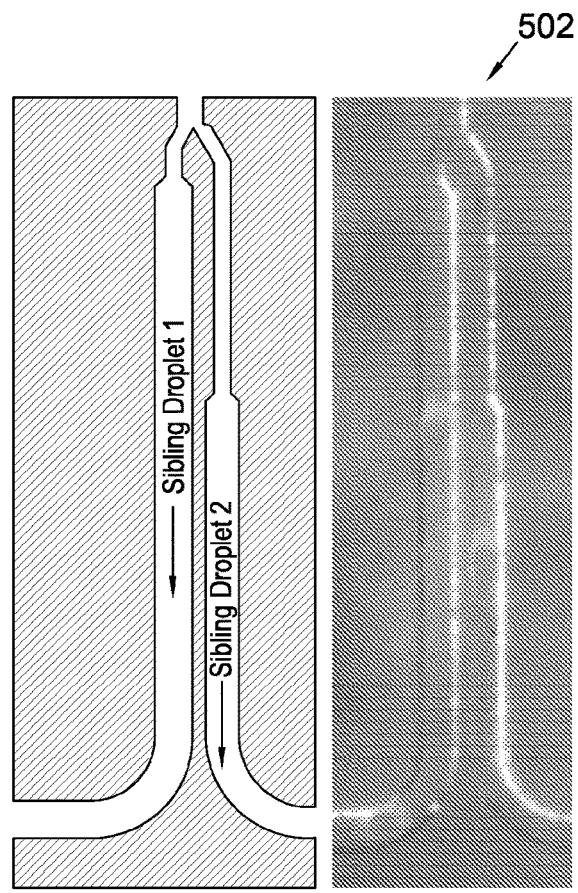
Fig.5a  Fig.5b
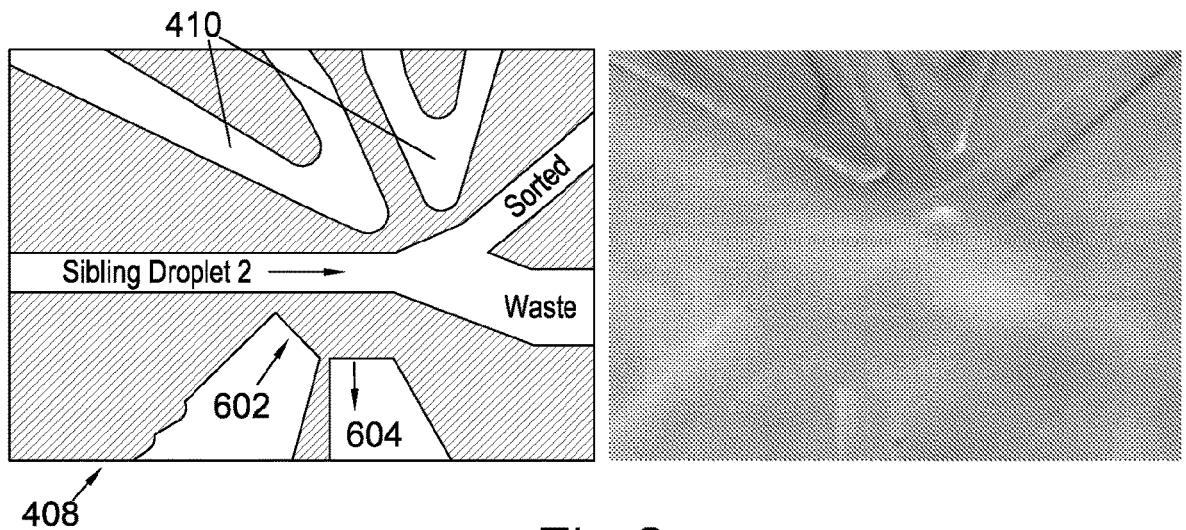
Fig.6

DROPLET SORTING BASED ON IONIZATION MASS SPECTROMETRY

CROSS REFERENCE TO RELATED APPLICATIONS

This application is a national phase application filed under 35 U.S.C. § 371 of PCT Application Number PCT/GB2015/052301 filed on 7 Aug. 2015 and titled "Droplet Sorting," which claims priority from G.B. Application No. 1414177.4 filed 11 Aug. 2014.

FIELD OF THE INVENTION

This invention generally relates to methods and systems for sorting a droplet, in particular in a microfluidic device. In a further aspect the invention relates to a microfluidic chip for splitting and sorting droplets.

BACKGROUND TO THE INVENTION

Mass spectrometry has widely been used to analyse and identify constituents of a sample of material. The material to be analysed is transferred into a gas phase and ionised. These ions are then accelerated via an electric field and sorted depending on their mass-to-charge ratio under the influence of a magnetic field.

US 2003/0136904 A1 specifies a liquid chromatograph mass spectrometer in which a droplet is ionised using electrospray ionisation and/or atmospheric pressure chemical ionisation. Constituents of the droplet are then analysed in a mass spectrometer. Further prior art can be found in US 2011/107822 A1, US 2004/0026617 A1, US 2012/0217389 A1, WO 2012/001421 A1 and US 2012/0153143 A1.

However, there is a need for improved techniques for analysing constituents of a droplet.

SUMMARY OF THE INVENTION

According to a first aspect of the invention there is therefore provided a method comprising: providing a droplet comprising a plurality of constituents, splitting said droplet into a first droplet and a second droplet, wherein said first droplet comprises a first fraction of said plurality of constituents and said second droplet comprises a second fraction of said plurality of constituents, analysing said constituents of said first fraction of said plurality of constituents in said first droplet, and sorting said second droplet dependent on an outcome of said analysis.

The inventors have realised that analysing constituents of a droplet may be destructive and may therefore have a negative impact or even prevent a further analysis of the droplet. The method therefore allows for analysing a first droplet, potentially destructively, whilst sorting a second droplet, which may have identical or similar constituents and properties as that of the first droplet, for potential further analysis.

Methods and systems described herein therefore allow for producing first and second droplets from the same parent droplet, and an outcome of the analysis of the first droplet may determine if and/or how the second droplet is processed further, for example collected for analysis and/or extraction/replication of the contents.

In embodiments, sorting a droplet may comprise, for example, selectively changing a flow or travel direction of a droplet, adjusting or regulating a flow or travel direction of a droplet, grouping droplets, classifying a droplet, dismissing/retaining a droplet, etc.

The skilled person will appreciate that a variety of properties of the constituents of the first fraction of the plurality of constituents in the first droplet may be of interest. These properties of the constituents may be, but are not limited to, the mass-to-charge ratio or the average mass-to-charge ratio, the size or average size, the weight or average weight, the chemical composition, or any other chemical or physical properties. It will be understood that certain properties of the constituents of the first fraction of the plurality of constituents in the first droplet may be of interest dependent on a further analysis or type of analysis intended to be performed on the second droplet. For example, the mass-to-charge ratio of the constituents of the first fraction of the plurality of constituents in the first droplet may be determined if the further analysis of the second droplet depends on what constituents are present in the first and second droplets. The skilled person will further appreciate that not only a single property, but two or more properties of the constituents of the first fraction of the plurality of constituents in the first droplet may be of interest.

Therefore, in a preferred embodiment of the method, the analysis of the constituents of the first fraction of the plurality of constituents in the first droplet comprises ionising the constituents of the first fraction of the plurality of constituents in the first droplet, and measuring a mass-to-charge ratio of the ionised constituents.

The second droplet may in some embodiments only be sorted if one or more conditions upon analysing the first droplet or constituents of the first droplet are met. If the one or more conditions are not fulfilled, the second droplet may merely be put to waste or processed further independently from the analysis of the first droplet.

Therefore, in a preferred embodiment of the method, the second droplet is sorted if the measured mass-to-charge ratio of a said ionised constituent coincides with a pre-defined mass-to-charge ratio or with one of a plurality of pre-defined mass-to-charge ratios. A plurality of pre-defined mass-to-charge ratios may be preferable over a single pre-defined mass-to-charge ratio because two different ionised constituents may give rise to a different mass-to-charge ratio signal if they carry a different amount of charges even if the chemical structure and composition of the two ionised constituents, and therefore their masses, are essentially identical. The mass of a single charge, i.e. a single electron (or electron-hole), is negligible compared to the mass of the ion. Hence, in order to identify and quantify a certain constituent in the first droplet, it may be preferable to compare the measured mass-to-charge ratio to a plurality of pre-defined mass-to-charge ratios.

Some ionised constituents, for example ionised molecules, may be identical with the exception of a single atom (or a small number of atoms) which may vary from one molecule to another. In such circumstances, the mass-to-charge ratio may differ only slightly from one of the constituents of the first droplet to another of the constituents of the first droplet. However, it may be preferable to sort the second droplet if the measured mass-to-charge ratio of a constituent in the first droplet coincides with a pre-defined mass-to-charge ratio of an ionised constituent in which only one or a few atoms vary from one constituent to another.

Therefore, in a preferred embodiment of the method, the pre-defined mass-to-charge ratio or plurality of pre-defined mass-to-charge ratios comprise a range or plurality of ranges of mass-to-charge ratios, respectively.

The second droplet may in some preferred embodiments only be sorted if a certain condition (or plurality of conditions) has (have) been met a pre-defined number of times.

Therefore, in some preferred embodiments of the method, the measuring comprises measuring an intensity of the measured mass-to-charge ratio of the ionised constituents above or below a pre-defined threshold intensity and/or measuring a pre-defined signal mass spectrometer pattern change across a plurality of ionised constituents. Hence, the second droplet may only be sorted if the measured mass-to-charge ratio(s) of the constituents in the first droplet give(s) rise to an intensity which exceeds or is below a predefined threshold intensity and/or upon showing a specific, pre-defined mass spectrometer pattern change across a plurality of ionised constituents. This may be particularly useful if the sorting and/or further analysis of the second droplet is only desired if a pre-defined amount or concentration of a certain constituent or plurality of constituents in the second droplet is required. Therefore, using embodiments described herein may allow for selecting a second droplet if an increase or decrease in level of a single constituent, and/or an overall change in the levels of a plurality of constituents is desired.

In some embodiments the second droplet may only be sorted if the measured mass-to-charge ratio of a first constituent in the first droplet gives rise to an intensity which exceeds a pre-defined threshold intensity for the first constituent, while the measured mass-to-charge ratio of a second constituent in the first droplet gives rise to an intensity which is below a pre-defined threshold intensity for the second constituent. This may be particularly useful if sorting and/or analysing the second droplet are only desired if the concentrations of the first and second constituents in the droplet are above and below pre-defined concentrations, respectively. This may, for example, allow for preventing an effect of a potential presence of the second constituent on the first constituent in the droplet. Such an effect may be undesired when the second droplet is analysed.

The skilled person will appreciate that if the analysis of the constituents of the first fraction of the plurality of constituents in the first droplet comprises ionising the constituents and measuring a mass-to-charge ratio of the ionised constituents, ionisation may be performed using a conventional method. These methods include, but are not limited to, electrospray ionisation, atmospheric pressure (chemical) ionisation, gas-phase ionisation, electron impact ionisation, chemical ionisation, and the like. It will be understood that each of the various methods for ionising constituents in the first droplet has advantages and disadvantages, and certain methods may be preferred over others depending on known and/or anticipated properties of the constituents in the first droplet. The skilled person will appreciate that ionisation of the constituents and measuring their mass-to-charge ratios may be performed in a standard, commercially available mass spectrometer which may incorporate ionisation means.

As the analysis of the constituents in the first droplet may be destructive, such that a further analysis is affected or not possible, it may be preferable to analyse the constituents of the first droplet in a region which is remote from the region where the second droplet is sorted.

Therefore, in a preferred embodiment of the method, the constituents of the first fraction of the plurality of constituents in the first droplet may be analysed in a first region, and the second droplet may be sorted in a second region which is remote from the first region. It will be appreciated that depending on the type of analysis to be performed on the constituents of the first droplet, further shielding or protection means may be provided to prevent the second droplet from being affected by the analysis of the constituents in the first droplet.

It will be understood that a droplet may be sorted using one of a variety of techniques. Such techniques include, but are not limited to, dielectrophoresis, magnetophoresis, electro-osmosis, and the like.

Therefore, in a preferred embodiment of the method, the second droplet is sorted by dielectrophoresis. In some further preferred embodiments, optical dielectrophoresis may be used to sort the second droplet if the droplet comprises a photoconductive material. The skilled person will appreciate that depending on the identified constituents, some techniques for sorting the second droplet may be preferred over others in order to minimise or prevent a negative impact on the droplet during the sorting process.

In some preferred embodiments of the method, the sorted second droplet may be stored and/or analysed after being sorted. Due to the analysis of the constituents of the first droplet, constituents in the second droplet are known, and do not need to be determined in a potentially destructive analysis prior to further analyses performed on the second droplet.

Embodiments described herein may be applicable to various kinds of droplets. Droplets to be analysed and/or sorted may be, for example, microdroplets or picodroplets. In some preferred embodiments of the method, the droplet(s) has (have) a diameter of less than 300 µm, preferably less than 100 µm, more preferably less than 75 µm, 65 µm or 50 µm. Depending on the types of analysis and measurements to be performed on the first and second droplets, the splitting of the (parent) droplet may be adjusted to control the size of the resulting first and second droplets.

In some preferred embodiments of the method, the plurality of constituents comprises analytes and/or biomolecules and/or metabolites. As the constituents in the second droplet may be sorted and/or analysed non-destructively, the methods described herein may be particularly useful for sorting and/or analysing biological material.

In some preferred embodiments of the method, the first fraction of the plurality of constituents and/or the second fraction of the plurality of constituents comprise a single cell and/or one or more cell populations. The method may be particularly suitable for sorting a single cell, or cells in general, because a destructive first analysis of a single cell would likely mean that a further analysis of the single cell in its original state is not possible.

Embodiments of the method described herein may be applied to a plurality of droplets in a single session, for example for quantification or reproducibility purposes. In order to analyse a plurality of droplets, it may be preferable to separate the droplets from each other.

Therefore, in some preferred embodiments of the method, providing the droplet comprises providing a plurality of droplets, wherein a droplet of the plurality of droplets is separated from a neighbouring droplet of the plurality of droplets by a first spacing fluid. Once the droplets are split, a said first droplet may then be separated from a neighbouring said first droplet by a second spacing fluid, and a said second droplet may be separated from a neighbouring said second droplet by a third spacing fluid.

It will be appreciated that the first, second and third spacing fluids may in fact be the same, single spacing fluid. Alternatively, the first, second and third spacing fluids may be different spacing fluids. The type of spacing fluid used for (parent) droplets, first droplets and second droplets may be chosen dependent on the properties of the droplets and/or the type(s) of analysis performed on the droplets since a spacing fluid may impede on a particular type of analysis of the droplets. In some embodiments, the first and/or second spacing fluids may be removed before analysing the first droplets and/or before sorting or analysing the second droplets.

In some preferred embodiments of the method, the first, second and third spacing fluids may be oils and/or water-in-oil emulsions.

In some further preferred embodiments of the method, the sorting of the second droplet may be performed in tandem with the analysis of the constituents of the first droplet, or with a known time delay between the sorting of the second droplet and the analysis of the constituents of the first droplet. Sorting the second droplet essentially simultaneously with the analysis of the constituents of the first droplet may be preferable if, for example, a change in property of the first and second droplets, for example, a degradation, is observed over time. The second droplet may then be sorted and potentially further analysed while being in the same or similar state as that of the first droplet when the latter is being analysed.

Methods and systems described herein may therefore allow for a label-free analysis and/or sorting of samples, for example in a cell, engineered molecule or synthetic biology library.

In a further aspect the invention provides a system comprising: a droplet splitting module for splitting a droplet into a first droplet and a second droplet, wherein said droplet comprises a plurality of constituents, and wherein said first droplet comprises a first fraction of said plurality of constituents and said second droplet comprises a second fraction of said plurality of constituents, an analyser for analysing said constituents of said first fraction of said plurality of constituents in said first droplet, a droplet sorting module for sorting said second droplet, and a feedback system in communication with said analyser and said droplet sorting module, wherein said feedback system is configured to control said sorting of said second droplet in said droplet sorting module dependent on an outcome of said analysis of said constituents of said first fraction of said plurality of constituents in said first droplet in said analyser.

As outlined above, in a preferred embodiment of the system, the analyser may comprise a mass spectrometer, in particular an electrospray ionisation mass spectrometer configured to ionise the constituents of the first fraction of the plurality of constituents in the first droplet and measure a mass-to-charge ratio of the ionised constituents.

In a preferred embodiment of the system, the droplet sorting module sorts the second droplet if the mass-to-charge ratio of the ionised constituents measured in the mass spectrometer coincides with a pre-defined mass-to-charge ratio or with one of a plurality of pre-defined mass-to-charge ratios. As outlined above, in a preferred embodiment, the pre-defined mass-to-charge ratio or plurality of pre-defined mass-to-charge ratios comprise a range or plurality of ranges of mass-to-charge ratios, respectively.

It will be appreciated that a variety of techniques may be used to split the droplet into first and second droplets. These techniques include, but are not limited to, geometry-mediated splitting, or droplet splitting using electric field, heat or lasers. It will be understood that one technique may be preferable over another dependent on the type of droplet(s) to be split.

In a preferred embodiment of the system, the feedback system initiates a sorting of the second droplet in the droplet sorting module if the measured mass-to-charge ratio of the ionised constituents gives rise to a signal with an intensity which is above or below a pre-defined threshold intensity and/or if the measured-mass-to-charge ratio of the ionised constituents shows a specific, pre-defined signal mass spectrometer pattern change across a plurality of ionised constituents. As described above, this may be preferable if a sorting and/or further analysis of the second droplet is only desired if, for example, the concentration of a constituent or plurality of constituents exceeds or is below (a) pre-defined threshold value(s).

The second droplet may be sorted in the droplet sorting module using a variety of techniques. The droplet sorting module may in some preferred embodiments be configured to sort the second droplet using dielectrophoresis. It will be understood that the droplet sorting module may be configured to sort the second droplet using a technique which depends on an outcome of the analysis of the constituents in the first droplet in the analyser. In other words, one sorting technique may be preferable over another technique dependent on a property (or plurality of properties) of the droplets as analysed in the analyser. Furthermore, in some embodiments, the droplet sorting module may be configured to switch from one sorting technique to another technique for different (second) droplets depending on an outcome of the analyses of their corresponding first droplets. The skilled person will appreciate that two or more techniques for sorting the second droplet may be exploited in the droplet sorting module dependent on an outcome of the analysis of the first droplet in the analyser.

In a preferred embodiment, the system further comprises a container for storing the sorted second droplet, and/or a measuring instrument for analysing the sorted second droplet.

As outlined above, if a plurality of droplets is to be split, analysed and sorted depending on an outcome of the analysis of the first droplets, one or more spacing fluids may be provided which separate the various droplets from each other. Therefore, in a preferred embodiment, the system further comprises a first spacing fluid to separate a droplet from a neighbouring droplet, a second spacing fluid to separate a first droplet from a neighbouring first droplet, and a third spacing fluid to separate a second droplet from a neighbouring second droplet. The first, second and third spacing fluids used in the system may be oils and/or water-in-oil emulsions. It will be understood that whether an oil or a water-in-oil emulsion is preferable for separating each of the parent droplets, the first droplets and the second droplets, may depend on the type of analysis and/or sorting performed on the droplets. As outlined above, in some preferred embodiments, means may be provided to remove the first and/or second spacing fluids before analysing the first droplets and/or before sorting or analysing the second droplets.

It may be preferential to sort the second droplet in the droplet sorting module in tandem with the analysis of the first droplet in the analyser. Therefore, in a preferred embodiment of the system, the feedback system is further configured to initiate the sorting of the second droplet in the droplet sorting module in tandem with the analysis of the constituents of the first fraction of the plurality of constituents in the first droplet in the analyser. Additionally or alternatively, the system may further comprise a delay line such that the second droplet is sorted in the droplet sorting module in tandem with the analysis of the constituents of the first fraction of the plurality of constituents in the first droplet. The delay line may allow for the second droplet to be transported to the droplet sorting module such that the second droplet arrives at the droplet sorting module at essentially the same time as the first droplet arrives at the analyser.

In some embodiments, the delay line may be designed such that the second droplet takes a longer time to reach the droplet sorting module than the first droplet takes to be analysed. This allows sorting of the second droplet based on the (preceding) analysis of the first droplet in the analyser.

It will be understood that the delay line may be incorporated between the droplet splitting module and the droplet sorting module, or between the droplet splitting module and the analyser, or between the droplet splitting module and the droplet sorting module as well as the droplet splitting module and the analyser.

If a plurality of droplets is provided to the droplet splitting module, it may be necessary to sequence the second droplets upon an analysis of the first droplets in the analyser. The skilled person will appreciate that a variety of techniques may be exploited to sequence the second droplets. Therefore, in a preferred embodiment, the system further comprises one or more optical fibres for sequencing the second droplets upon analysing the constituents of the first fraction of the plurality of constituents in the first droplet in the analyser. It will be understood that other optical elements may be exploited for optical interrogation of the droplets. In another preferred embodiment, the system further comprises an imaging system for sequencing the second droplets upon analysing the constituents of the first fraction of the plurality of constituents in the first droplet in the analyser.

Depending on the type of analysis performed on the first and second droplets, some or all of the features of the system described herein may be incorporated into a chip, for example a microfluidic chip.

There is therefore provided a microfluidic chip, the chip comprising the droplet splitting module and the droplet sorting module. The chip may further comprise a first channel which connects the droplet splitting module with the analyser for guiding the first droplet(s) from the droplet splitting module to the analyser. The chip may further comprise a second channel which connects the droplet splitting module and the droplet sorting module for guiding the second droplet(s) to the droplet sorting module. The microfluidic chip may further comprise a connector for connecting the droplet sorting module and the feedback system such that the feedback system may control the sorting of the second droplet(s) in the droplet sorting module.

The microfluidic chip may further comprise the one or more delay lines between the droplet splitting module and the droplet sorting module, as well as the droplet splitting module and the analyser, respectively. It will be understood that if the analyser is at a location remote from the microfluidic chip, the first channel on the chip may further comprise a connector for connecting the first channel, and therefore the droplet splitting module, with the analyser.

As outlined above, the second droplets may be sequenced upon analysing the constituents of the first fraction of the plurality of constituents in the first droplet in the analyser. Therefore, in a preferred embodiment, the microfluidic chip comprises one or more optical fibres and/or an imaging system which may be exploited for sequencing the second droplets. It will be understood that other optical elements may be incorporated on the microfluidic chip for optical interrogation of the droplets.

The (parent) droplets may be kept in a reservoir prior to being transported to the droplet splitting module. It may therefore be necessary to generate individual droplets which are to be split into first and second droplets. Hence, in a preferred embodiment, the microfluidic chip further comprises means for generating a droplet. The microfluidic chip may further comprise the reservoir for storing the parent droplets.

In order to store the spacing fluids used to separate a parent droplet from a neighbouring parent droplet, a first droplet from a neighbouring first droplet and a second droplet from a neighbouring second droplet, one or more further reservoirs may be provided. In a preferred embodiment, the microfluidic chip comprises one or more reservoirs for storing the spacing fluids. The microfluidic chip may comprise further channels for providing the spacing fluids to the various parts of the system where two or more droplets are provided or generated.

As outlined above, the sorted second droplet(s) may be stored in a container prior to further analysis. Therefore, in a preferred embodiment, the microfluidic chip further comprises a (or the above-described) container for storing the sorted second droplet.

In a preferred embodiment, one or both of the droplet splitting module and the droplet sorting module may be implemented in a microfluidic chip, wherein the microfluidic chip optionally further comprises one or more of: a first channel connecting the droplet splitting module and the analyser for guiding a said first droplet from the droplet splitting module to the analyser, a second channel connecting the droplet splitting module and the droplet sorting module for guiding a said second droplet from the droplet splitting module to the droplet sorting module, and a connector for connecting the droplet sorting module and the feedback system. Additionally or alternatively, in some preferred embodiments, the analyser and/or the feedback system may be implemented on the microfluidic chip.

In embodiments of the methods and systems described herein, an emulsion comprising aqueous droplets stabilised in oil with surfactants may be provided. The use of surfactants may, for example, stabilise the droplets (before and after splitting) against coalescence as they may reside at the interface between the water and the oil and thereby reduce the oil-water interfacial tension.

In a related aspect of the invention, there is provided a method for aligning sequences of streams comprising droplets, the method comprising: providing an emulsion comprising a plurality of target droplets and a plurality of tag droplets, wherein a said tag droplet comprises a first tag and a second tag; splitting a said target droplet into a first target droplet and a second target droplet and splitting a said tag droplet into a first tag droplet and a second tag droplet, wherein both said first tag droplet and said second tag droplet comprise said first tag and said second tag; providing a said first target droplet and a said first tag droplet into a first stream of droplets, and providing a said second target droplet and a said second tag droplet into a second stream of droplets; detecting said first tag droplets (and preferably said first target droplets) in said first stream and detecting said second tag droplets (and preferably said second target droplets) in said second stream; determining a first sequence of droplets in said first stream based on said detection of said first tag droplets (and preferably said first target droplets) and determining a second sequence of droplets in said second stream based on said detection of said second tag droplets (and preferably said second target droplets); and comparing said determined first and second sequences to align said first and second sequences.

Embodiments of the method may be combined with any of the above-described embodiments of methods and systems, for example, for analysing constituents of a first sibling droplet and sorting a second, corresponding sibling droplet dependent on an outcome of the analysis of the first sibling droplet.

Embodiments of the method for aligning sequences of streams comprising droplets may therefore ensure that the correct sibling droplets are correlated.

In embodiments, the target and tag droplets may simply be identified (or counted) to obtain binary code sequences for droplets in the first stream and in the second stream, respectively. A "1" may thereby, for example, correlate to a tag droplet being detected, while a "0" may refer to a target droplet being detected (or vice versa). The binary code sequences of droplets in the first and second stream may then be compared to each other to align the sequences accordingly (for example by buffering portions of the respective sequences in memory).

It will be appreciated that upon splitting a (parent) tag droplet, the first tag droplet as well as the second tag droplet may comprise both of first and second tags. The presence of the first tag has no (or no detrimental) effect on the detection of the second tag in the second stream. Similar considerations apply to the presence of the second tag when the first tag is being detected in the first stream.

It will be understood that in embodiments, the first tag droplet and the second tag droplet each comprises a plurality of first and second tags.

The target droplet may be, for example, a droplet comprising analytes, biomolecules and/or metabolites of interest.

In a preferred embodiment of the method, the first tag comprises a mass spectrometer tag, wherein the detection of the first tag droplet comprises detecting a mass-to-charge ratio of the mass spectrometer tag. The precision of a mass spectrometer, which is generally accurate to 1 atomic mass units (amu) or even less, therefore allows for a reliable identification of the first tag.

Preferably, a mass of the mass spectrometer tag is within +/−5000 amu of the mass-to-charge ratio of a constituent of the target droplet, preferably within +/−500 amu, more preferably within +/−50 amu. As outlined above, a mass spectrometer may generally be accurate to 1 amu or even less. Therefore, a mass spectrometer tag of the first tag droplet may be distinguished in the mass spectrometer from a target droplet (e.g. analyte, biomolecule or metabolite droplet) when the mass spectrometer tag gives rise to a mass-to-charge ratio which is only slightly different from that of a target droplet. However, the larger the range of mass-to-charge ratios which are being detected in the mass spectrometer, the larger the data sets are which are obtained via the mass spectrometer measurements. By providing mass spectrometer tags with mass-to-charge ratios which are within the above-identified preferred ranges, the mass spectrometer data sets may advantageously be reduced significantly. A reduced data set may further allow for a higher throughput of droplets in the mass spectrometer, and therefore a higher throughput of droplets which are to be sorted in the droplet sorting unit.

In a further preferred embodiment of the method, the second tag comprises a fluorescent tag, wherein the detection of the second tag droplet comprises one or both of detecting a fluorescence level of the fluorescent tag and detecting a fluorescence wavelength of the fluorescent tag. Embodiments of the method may therefore allow for an accurate detection of the second tag based on, e.g. a combination of parameters of the properties of the second tag. In embodiments detection of the second tag droplets also comprises detecting scattered light derived from incident light scattered from the second tag droplets; and preferably then detection of the second target droplets comprises detecting scattered light derived from incident light scattered from the second target droplets.

The fluorescent tag may be, for example, a fluorescent nanoparticle, a fluorescent bead, a fluorescently labelled macromolecule, a fluorescent organic dye, and others.

In more sophisticated embodiments of the method the detection of the first tag droplet comprises assigning a first code to a said first tag droplet dependent on the mass-to-charge ratio, and the detection of the second tag comprises assigning a second code to a said second tag droplet dependent on one or both of a the fluorescence level and the fluorescence wavelength. The comparing may then comprises comparing the first and second codes. That is, for example, the mass spec and optical tags may each encode a numeric value (other than a binary 1/0) and these values may then be correlated. By identifying and correlating the two codes obtained using embodiments of the method, the first and second sequences may be aligned to reliably identify droplets stemming from the same (parent) droplet.

In a related embodiment of the method, the tag droplets of the plurality of tag droplets may be distinguishable from each other via a concentration of a said second tag in a said droplet. That is, for example the optical tag may have a fluorescence intensity (for a given droplet volume) which may be varied to encode a value. In principle encoding values into tags in this way may facilitate sequence alignment (for example allowing alignment with shorter read sequences).

In a preferred embodiment of the method, a ratio of the target droplets to the tag droplets in the emulsion is larger than 1:1, preferably larger than 5:1, more preferably larger than 10:1. A too large relative number of tag droplets in the emulsion would not be commercially viable since a relatively small number of target droplets would be identified and sequenced. However, if the relative number of tag droplets were below a threshold, it may be difficult to align the first and second sequences.

In a related aspect of the present invention, there is provided a droplet splitting module for splitting a droplet into a first droplet and a second droplet, the droplet splitting module comprising: an inlet channel; and a plurality of outlet channels; wherein a first said outlet channel has a first channel width variation in a downstream direction of said first outlet channel configured to generate a first back-pressure in said first outlet channel; and wherein a second said outlet channel has a second channel width variation in a downstream direction of said second outlet channel configured to generate a second back-pressure in said second outlet channel; and wherein a ratio between a volume of said first droplet and a volume of said second droplet is controllable by controlling a ratio between said first back-pressure and said second back-pressure.

It may be desirable to split a (parent) droplet such that a relatively small-sized (first) droplet may be analysed, for example in a mass spectrometer. The volume of the first droplet may thereby be sufficiently large such that the droplet may be analyser in the mass spectrometer. This allows for sorting and processing a second droplet stemming from the parent droplet whereby the second droplet contains a majority or most of the material (analyte, biomolecule, etc.) of interest.

The droplet splitting module may be incorporated in any of the above-described embodiments of the system and the microfluidic chip.

We also describe a method of aligning two sequences, a first sequence (A) of tagged and target droplets, and a second sequence (B) of tagged and target droplets. The first sequence (A) may be provided to a device which has a destructive droplet interrogation process, such as a mass spectrometer; the second sequence (B) may be presented to a non-destructive droplet interrogation system such as an optical tag reading system. Droplets from the second sequence may be collected for later processing (for example analysis and/or replication of the contents). The contents of a collected droplet may be known/identified from the mass spectrometer if the droplet sequences are aligned so that a droplet in one sequence can be paired with a "sibling" drop in the other sequence. The mass spectrometer tag may comprise a molecular marker with a distinguishable mass: charge ratio (m/z); the optical tag may comprise a fluorescent molecule (which may be the same molecule as the mass spectrometer tag). A population of tagged droplets is mixed with the target droplets and droplets progress through the microfluidics system in an approximately random order as regards whether or not a droplet in a sequence is tagged (though preferably overall the tagged droplets make up less than half the total population).

One procedure for aligning the sequences involves identifying and matching strings of values, preferably binary values such as 1s or 0s, in each sequence. Thus one binary value, say 0, identifies a tagged droplet and another value, say 1, identifies a (potential) target droplet. In embodiments a tagged droplet binary value may be assigned to a droplet in the optical sensing fluid flow path by identifying whether or not a droplet fluoresces (fluorescence may, for example, be given a 0 value); however other optical signals may alternatively be employed. In embodiments a tagged droplet binary value may be assigned to a droplet in the fluid flow path to the mass spectrometer by identifying whether or not the contents of a droplet have a mass:charge ratio (m/z) which identifies the molecular marker (in which case the droplet may, for example, be given a 0 value). However it can be useful to actively assign a binary value to mass spectrometer measurement, so that target droplets are actively given a binary value (such as 1), rather than merely relying on the absence of a tagged droplet. In this case a target droplet may be assigned a target droplet binary value (such as 1) based on detection of a mass:charge ratio (m/z) which identifies the expected target constituent(s) of a droplet. The skilled person will appreciate that the molecular marker will have a specific, identifiable mass:charge ratio (m/z) whereas typically it is possible to identify one or more constituents of the target droplets which have a different specific, identifiable mass:charge ratio (m/z).

The skilled person will appreciate that there are many ways of aligning the two sequences. In one approach run lengths of one or other (or both) binary values are determined and matched to align the sequences. For example binary 0 run lengths of, say, 3, 7, 9 may be identified in both sequences and then the starting droplets of each sequence identified as sibling droplets.

In one implementation a count is made of the lengths of sequences of 0s (or 1s) by resetting a counter when a marker or tag binary value is identified and then incrementing a counter each time a target droplet is detected, until the next marker or tag binary value is identified, when a record is made of the count and the counter reset once more.

The techniques described above are robust to errors in droplet interrogation, which is advantages as the throughput of a system may be of order 1-10 kilodroplets/sec, and many millions of droplets may be processed.

Thus in a related aspect of the present invention, there is provided an algorithm, which enables to identify a said second droplet of interest and to be sorted in the said sorting module having a measured intensity of the said measured mass-to-charge ratio of said constituents above a pre-defined threshold intensity in a said first droplet from the same said droplet, comprising:
  detecting a sequence A, which comprises a string of, in a random order,
    a plurality of Zeros A, at which a Count A is reset to zero; and
    a plurality of Counts A, which a said Count A starts from 1 at the first Count A after a said Zero A, and then adds one integer unit on the next Count A, and progresses until meeting with another Zero A;
  detecting a sequence B which comprises, in the substantially same order as the said Detection A,
    a plurality of Zeros B, at which a Count B is reset to zero;
    a plurality of Counts B, which the said Count B starts from 1 at the first Count
    B after a said Zero B, and then adds one integer unit on the next Count B,
    and progresses until meeting with another Zero B;
  synchronizing detected sequences A and B using the counts.

In a preferred embodiment, Zero A is assigned to a plurality of first marker droplets, which contain an organic or an inorganic molecule and a reagent;
  the organic or inorganic molecule have a mass-to-charge ratio different from the said measured mass-to-charge ratio of the said constituents in the said first droplet, and in the region within +/−5000 amu of the said constituents in the said first droplet, preferably within +/−500 amu of the said constituents in the said first droplet, and more preferably within +/−50 amu of the said constituents in the said first droplet;
  the reagent is from, but limited to, quantum dot (1-10 nm diameter), quantum dot labelled bead (e.g. latex bead, silica gel bead, magnetic bead ect, 0.01-15 μm diameter), fluorescent bead (0.01-15 μm), a fluorescently labelled macromolecule (e.g. protein, polysaccharide etc.);
the said first marker droplets are identified by the detection of the said mass-to-charge ratio of the said organic or inorganic molecule with the said analyser.

In a further preferred embodiment, Count A is assigned to the said first droplets after analysed the said mass-to-charge ratio, in the said analyser, of the said constituents in the said first droplet.

In a preferred embodiment, Zero B is assigned to a plurality of second marker droplets, which contain a reagent and an organic or an inorganic molecule;
  the reagent is from, but limited to, quantum dot (1-10 nm diameter), quantum dot labelled bead (e.g. latex bead, silica gel bead, magnetic bead ect, 0.01-15 μm diameter), fluorescent bead (0.01-15 μm), a fluorescently labelled macromolecule (e.g. protein, polysaccharide etc.) or an organic fluorescent dye, in the said marker droplets;
  the organic or inorganic molecule have a mass-to-charge ratio different from the said measured mass-to-charge ratio of the said constituents in the said first droplet, and in the region within +/−5000 amu of the said constituents in the said first droplet, preferably within +/−500 amu of the said constituents in the said first droplet, and more preferably within +/−50 amu of the said constituents in the said first droplet;

the said second marker droplets are identified by the detection of an optical signal from the said reagent in the said second marker droplets.

In a further preferred embodiment, Count B is assigned to the said second droplets which are lack of the said optical signal from the said reagent in the said second marker droplets.

In a preferred embodiment, Synchronization is to compare and match the pattern of the order of said Zero B and said Count B of said Detection B with the pattern of the order of said Zero A and said Count B of said Detection A.

In a preferred embodiment, the said first marker droplet and the said second marker droplet are generated from a maker droplet, which contain an organic or an inorganic molecule and a reagent;

the organic or inorganic molecule have a mass-to-charge ratio different from the said measured mass-to-charge ratio of the said constituents in the said first droplet, and in the region within +/−5000 amu of the said constituents in the said first droplet, preferably within +/−500 amu of the said constituents in the said first droplet, and more preferably within +/−50 amu of the said constituents in the said first droplet;

the reagent is from, but limited to, quantum dot (1-10 nm diameter), quantum dot labelled bead (e.g. latex bead, silica gel bead, magnetic bead ect, 0.01-15 μm diameter), fluorescent bead (0.01-15 μm), a fluorescently labelled macromolecule (e.g. protein, polysaccharide etc).

The invention further provides processor control code to implement the above-described systems and methods, for example on a general purpose computer system or on a digital signal processor (DSP). The code is provided on a non-transitory physical data carrier such as a disk, CD- or DVD-ROM, programmed memory such as non-volatile memory (eg Flash) or read-only memory (Firmware). Code (and/or data) to implement embodiments of the invention may comprise source, object or executable code in a conventional programming language (interpreted or compiled) such as C, or assembly code, or code for a hardware description language. As the skilled person will appreciate such code and/or data may be distributed between a plurality of coupled components in communication with one another.

The marker droplets are preferably mixed with the said droplets prior to analysing on the microfluidic chip described in embodiments herein.

In a preferred embodiment, the percentage of said marker droplets is less than 50% of the total combined number of the said marker droplets and the said droplets, preferably less than 20%, and more preferably less than 10% of the total combined number of the said marker droplets and the said droplets.

Embodiments of the method and system described herein may be exploited in a variety of fields, such as, but not limited to, disease diagnosis, drug discovery, cell therapeutics and the like.

BRIEF DESCRIPTION OF THE DRAWINGS

These and other aspects of the invention will now be further described, by way of example only, with reference to the accompanying figures in which:

FIG. 5a and FIG. 5b show schematic illustrations and optical images of droplet splitting modules according to embodiments of the present invention;

FIG. 6 shows a schematic illustration and an optical image of a droplet sorting unit according to embodiments of the present invention;

DETAILED DESCRIPTION OF PREFERRED EMBODIMENTS

Embodiments of the method and system described herein allow for splitting a (parent) droplet into first and second droplets, and analysing the first droplet, potentially destructively, whilst sorting the second droplet, which may have similar or identical constituents and properties as that of the first droplet, for potential further analysis.

Figure 1:
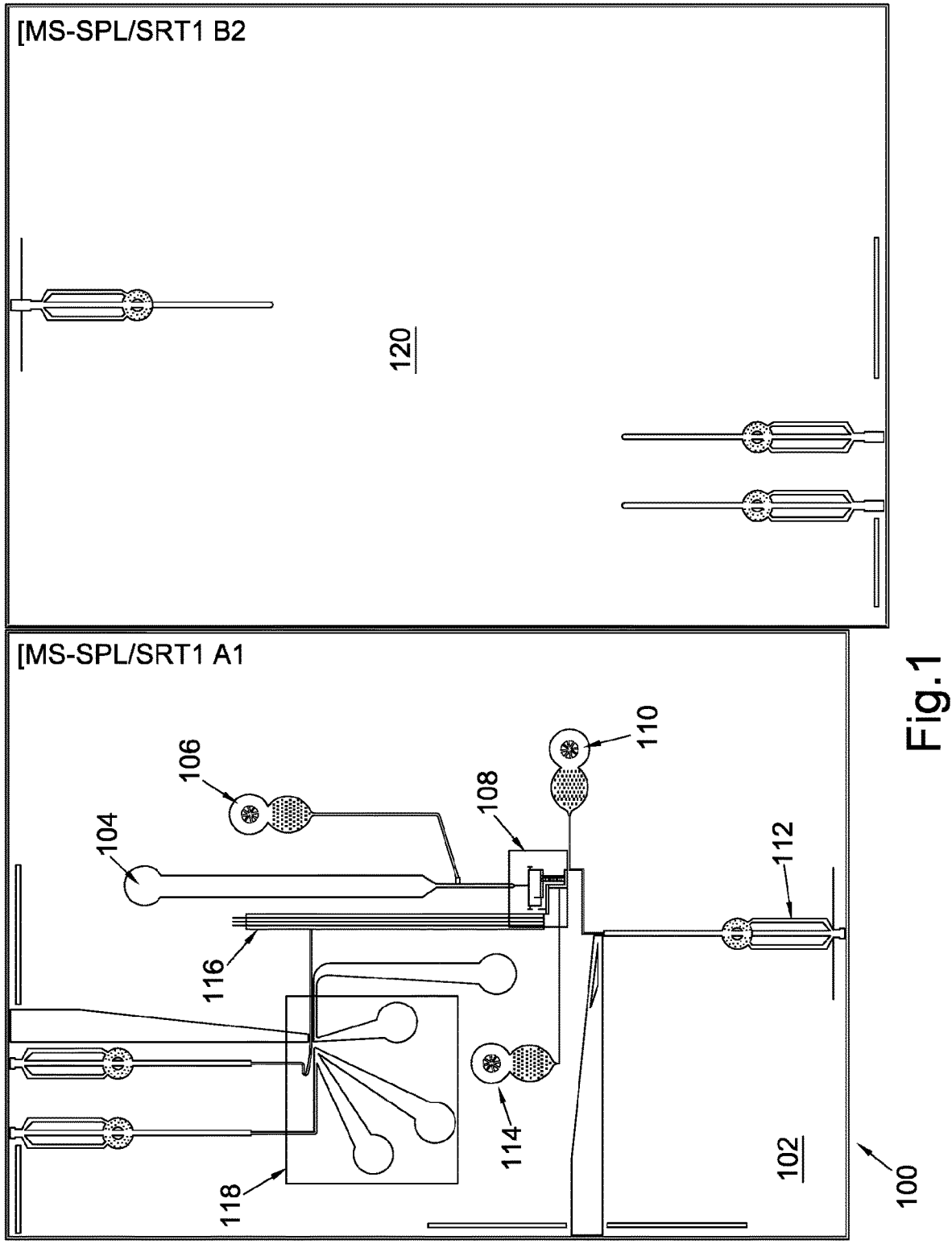
FIG. 1 shows a schematic illustration of a droplet splitting and sorting chip according to embodiments of the present invention.

As outlined in the summary part of this description, the system according to embodiments described herein may be (wholly or partly) provided on a microfluidic chip. FIG. 1 shows a schematic illustration of an example picodroplet splitting and sorting chip 100. The left-hand side of FIG. 1 shows a top section 102 of the chip 100, whereas the right-hand side of FIG. 1 shows a bottom section 120 of the chip 100.

The schematic illustration of the chip design shown in FIG. 1 incorporates a number of features, such as water-in-oil re-injection, picodroplet splitting and, dielectrophoretic sorting of (second) picodroplets. In this example, the chip 100 comprises a container 104 for storing an emulsion which contains the parent picodroplets to be split in the droplet splitting module 108. In order to separate the parent picodroplets from each other when they are provided to the droplet splitting module 108, spacing oil 106 is provided via an inlet connected to the channel between the emulsion container 104 and the droplet splitting module 108. In this example, a reservoir for spacing oil 106 is provided on-chip. Spacing oil 106 may further reduce the interfacial tension of the droplets.

A second spacing fluid, spacing oil 110, is provided which pushes the (first) picodroplets after splitting of the parent droplets into the mass spectrometer (not shown in FIG. 1). In this example, spacing oil 110 also reduces the interfacial tension of the (first) picodroplets. Furthermore, spacing oil 110 may induce cell lysis, reduce the required capillary voltage and minimise the number of charge states of a protein (e.g. 1,1,1-trifluoro-2-ethanol). Here, a reservoir for spacing oil 110 is provided on-chip.

A third spacing oil, spacing oil 114, is used for spacing the second droplets after splitting of the parent droplets. Spacing oil 114 may also increase the interfacial tension of the droplet to a level that allows it to be sorted, in this example, by the dielectrophoretic droplet sorting module 118. Spacing oil 114 may further be used to stabilise the picodroplets enough for individual genetic analysis at a later point in time.

In this example, the chip further comprises a fitting 112 for a mass spectrometer emitter so as to provide the first droplets to the mass spectrometer unit.

In this example, a delay line 116 is incorporated onto the chip 100. While the first picodroplet is guided to the mass spectrometer emitter for analysis of the constituents of the first picodroplet, the corresponding second picodroplet moves through delay line 116 to the droplet sorting module 118. The length of the delay line 116 is chosen in this example such that the second picodroplet arrives at the droplet sorting module 118 essentially simultaneously as the corresponding first picodroplet arrives at the mass spectrometer emitter.

The use of optical fibres on-chip allows the sequence of droplets to be counted in such a way that when a first droplet produces a favourable set of mass-to-charge ratio signals of appropriate intensity, the second droplet is actively sorted and may be retained for analysis, the analysis in this example being off-chip. It will be understood that other optical detection means may be used to allow for sequencing the second droplets.

In this example, some of the picodroplet channels as well as in- and outlets for picodroplets are provided on the bottom side 120 of chip 100.

As we have previously described in WO2012/001421, in embodiments the aqueous microdroplet may be, e.g., a ~2 nL-200 pL plug, which may have a diameter in the range of several (e.g., ~5 um-~10 um) to tens (e.g., ~20 um, ~50 um, greater than ~100 um) of microns, and/or may comprise one or more analytes, e.g., a single analyte or a mixture of analytes. The analyte may be fluorescent or non-fluorescent, and may comprise, e.g., chemical compounds such as for example an enzymatic assay (e.g., an embodiment may comprise assay compounds for their efficacy as enzyme inhibitors), DNA, protein, peptide, an organism such as a cell, and so forth.

The oil composition may comprise, e.g., fluorous and/or mineral oil, and, e.g., 25% vol/vol surfactant. A relatively low viscosity and/or light oil is preferable, for example since such oils generally have lower boiling points, which may be advantageous for evaporation from an ESI-MS emitter. More specifically, the ESI-MS advantageously uses a sprayable oil, preferably of low viscosity, low boiling point, i.e. suitable for evaporation from the emitter, e.g., a boiling point of ~100-~120 deg C. (similar to water), and/or that allows formation of a stable Taylor cone on the mass spectrometry emitter.

Preferably a surfactant is used to stabilise the aqueous microdroplet in the oil composition. The surfactant may comprise one or more surfactants, and may be a polymeric or a small molecule surfactant. Moreover, the surfactant may ionise relatively inefficiently (for example compared to the analyte). Such surfactants may have relatively poor surfactant properties, e.g., may be less good at preventing fusion of microdroplets, compared to other surfactants that are less suitable for mass spectrometry. For example, surfactants in an embodiment may comprise small molecules (e.g., having a molecular weight of less than 800 g/mol, more preferably less than 600 g/mol or 400 g/mol, e.g., 364 g/mol) and hence may be volatile. This may be advantageous for evaporation of the spray droplets allowing more charged analyte molecules to be in the gas phase for detection by the mass spectrometer.

In contrast to the above relatively poor surfactants, surfactants derived from block copolymers of perfluoroethers, e.g. Krytox™ and polyethyleneglycol (PEG) containing one or more amide linkages and with both variable geometry and morphology may be suitable. However, surfactants composed of fluorophilic and hydrophilic co-block polymers of the above type, which are linked together via amide bonds, can be of reduced utility due to significant suppression of the analyte(s) ions by those from the competing surfactant. These biocompatible di-block and tri-block amide based copolymers generally have more flexible chains that allow better packing at the interface. Also being polymeric, they generally pack a considerable depth of fluorous tail onto the interface of the droplet. This structure of a polar polymeric hydrophilic core with two polymeric fluorous tails on either end helps to stabilise the surface of the droplet hence stop them merging (a bit like bumpers on a car—they have some spring).

In contrast, fluoroalkyl chains as in 1H,1H,2H,2H-perfluorooctanol are more preferable in an embodiment as they are relatively rigid (but may be of too short a length to stop droplets coming into contact and coalescing). Such a molecule only has six carbons with fluorines attached, carbons 1 and 2 having hydrogens attached. This molecule also only has one hydroxyl group (i.e. a small polar head group) with a short rigid fluorous tail.

The surfactant preferably has a low boiling point, e.g., ~100-~120 deg C. similar to water, and is thus preferably a relatively light molecule. As indicated above, this may be advantageous for evaporation from the droplets that are sprayed from the emitter. More specifically, a suitable surfactant may be a molecule having a hydrophilic or polarised head end (e.g. alcohol, ether, ester, acid- or amine-based or some polymeric combination of these functional groups), and a fluorophilic (e.g. fluorocarbon) tail end. Good surfactants may be amide-based and/or polymeric, e.g., polyamide, but it has been found that in practice these also ionise well using the electrospray mass spectroscopy technique and so are overall less preferable. In some preferred implementations the tail may comprise a fluorinated chain (for example the surfactant may be a fluorocarbon) so that the tail end is fluorophilic; this is helpful for use with fluorous oils (e.g. perfluoroalklyamine oil). Various surfactants have allowed high analyte detection sensitivity in experiments, e.g., 1H,1H,2H,2H-perfluoro-1-octanol and pentadecafluorooctanoic acid. Because the preferred surfactants are relatively poor a relatively high concentration of surfactant may be needed, for example greater than 5%, 10%, 15%, 20%, 25% or 30% vol/vol or <5 mg/ml dependent on its structural type.

Preferably, the surfactant is less ionisable than the analyte. Similarly, the oil is preferably less ionisable than the analyte. The sign and magnitude of the ionisation potential difference is preferably such that ions produced from the oil and/or surfactant have opposite charge from the ionised analyte, or are neutral.

More specifically, the surfactant preferably has a higher ionisation potential relative to the analyte or analytes, e.g. such that the surfactant remains neutral and is not observed in the mass spectrometer, or is an acid or base which dissociates in solution to produce an ion which is oppositely charged to the sign of the potential difference applied to the emitter used to ionise the analyte. A greater proportion of available charge may then be available to allow ionisation of the analyte rather than the oil or surfactant during mass spectrometry.

In view of the poor surfactant used in embodiments, it may be advantageous to space the droplets or plugs in the channel out, separated evenly by oil, preferably to ensure that they pass through the channel into the emitter such that contact between them is reduced or substantially never occurs. This may be achieved by zero dead volume fitting to guide the droplets in to the lumen of the emitter.

Figure 2:
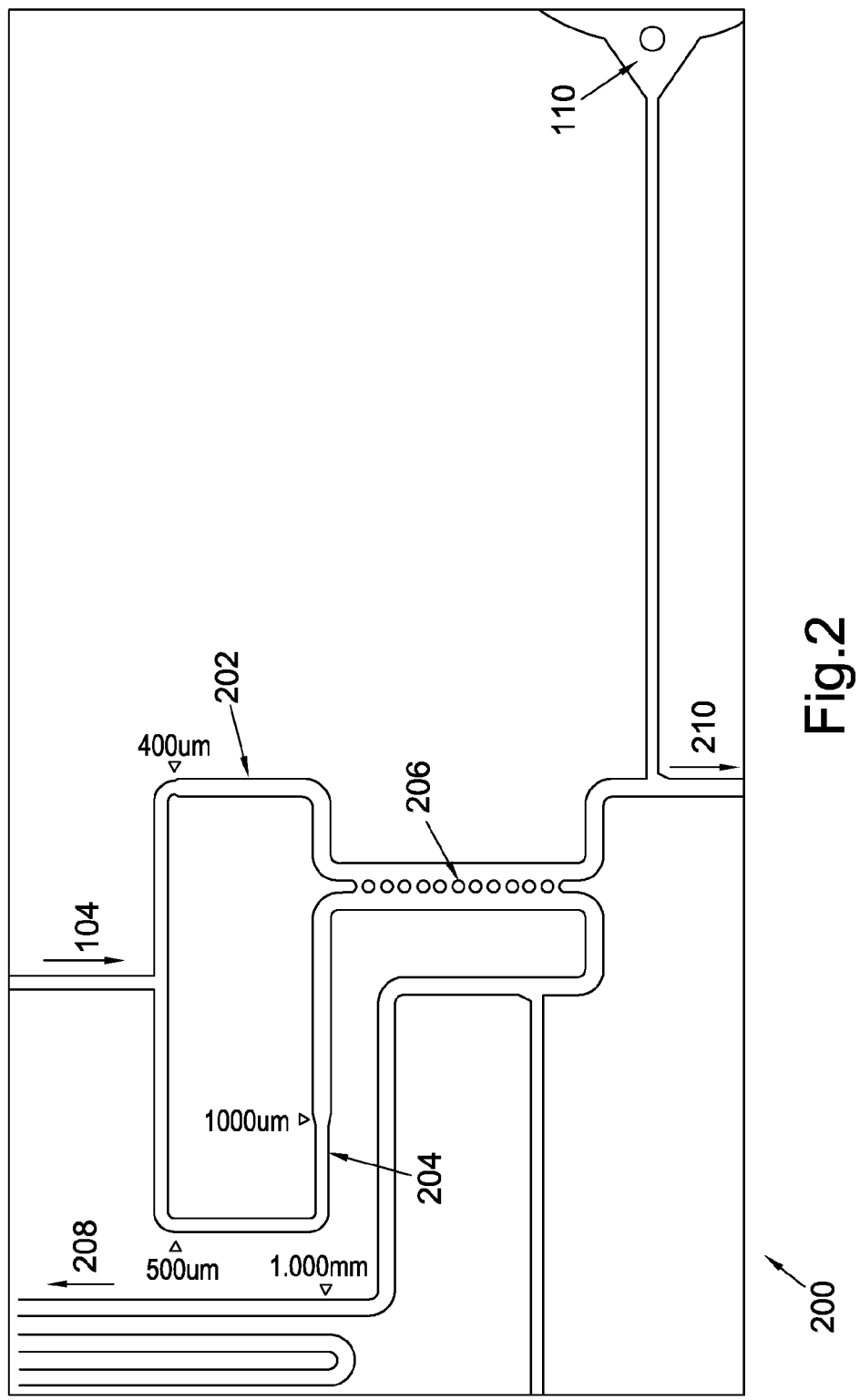
FIG. 2 shows a schematic illustration of a droplet splitting module according to embodiments of the present invention.

FIG. 2 shows a schematic illustration of a droplet splitting module according to an embodiment of the present invention. The splitting design used in this example is the passive droplet splitting module published by Jing Nie et al., "Sampling from Nanoliter Plugs via Asymmetrical Splitting of Segmented Flow", Anal. Chem., 2010, 82 (18), pp 7852-7856. This splitting design uses droplets generated on-chip as opposed to surfactant-stabilised droplets.

As shown in FIG. 2, the emulsion from container 104 comprising the parent droplets are pumped into a loop where a parent droplet splits according to the flow resistance of each arm of the loop. The loop structure may be preferably designed so as to avoid changes in flow resistance with time which may occur as a result of accumulation of droplets in the downstream paths. Pressure equalisation pillars 206 may be provided to enable the carrier emulsion to cross between the two downstream paths at the downstream junction to allow for pressure equalisation. At the same time, the pressure equalisation pillars 206 prevent droplets comprising constituents to be analysed from crossing the pillars such that coalescence of the droplets is avoided. Hence, a recombination of first and second droplets may be prevented.

The loop structure shown in FIG. 2 therefore allows for a stable splitting, i.e. splitting ratio, as the pressure in the two arms of the loop may be stabilised. The splitting is enhanced by providing narrowed paths (high pressure path 204 in FIG. 2) at the upstream junction of the loop which increases the flow rate and results in elongated droplets. A low pressure path 202 is provided via the other arm of the loop. An asymmetric splitting, if desired, may be achieved by providing different lengths of narrowed paths on each side of the loop. This may be particularly useful if only a small amount of the first droplet is needed for an initial, potentially destructive analysis, and the second droplet may comprise a larger amount of fluid (and therefore constituents) which may be employed in an analysis of the second droplet.

It will be understood that other droplet splitting module structures may be used to split the parent droplets into first and second droplets.

The first picodroplet is then, in this example, provided to the mass spectrometer, via path 210. The spacing oil 110 allows for separating the first droplets in the path 210. The second droplets are provided to the delay line 116 via path 208.

Figure 3:
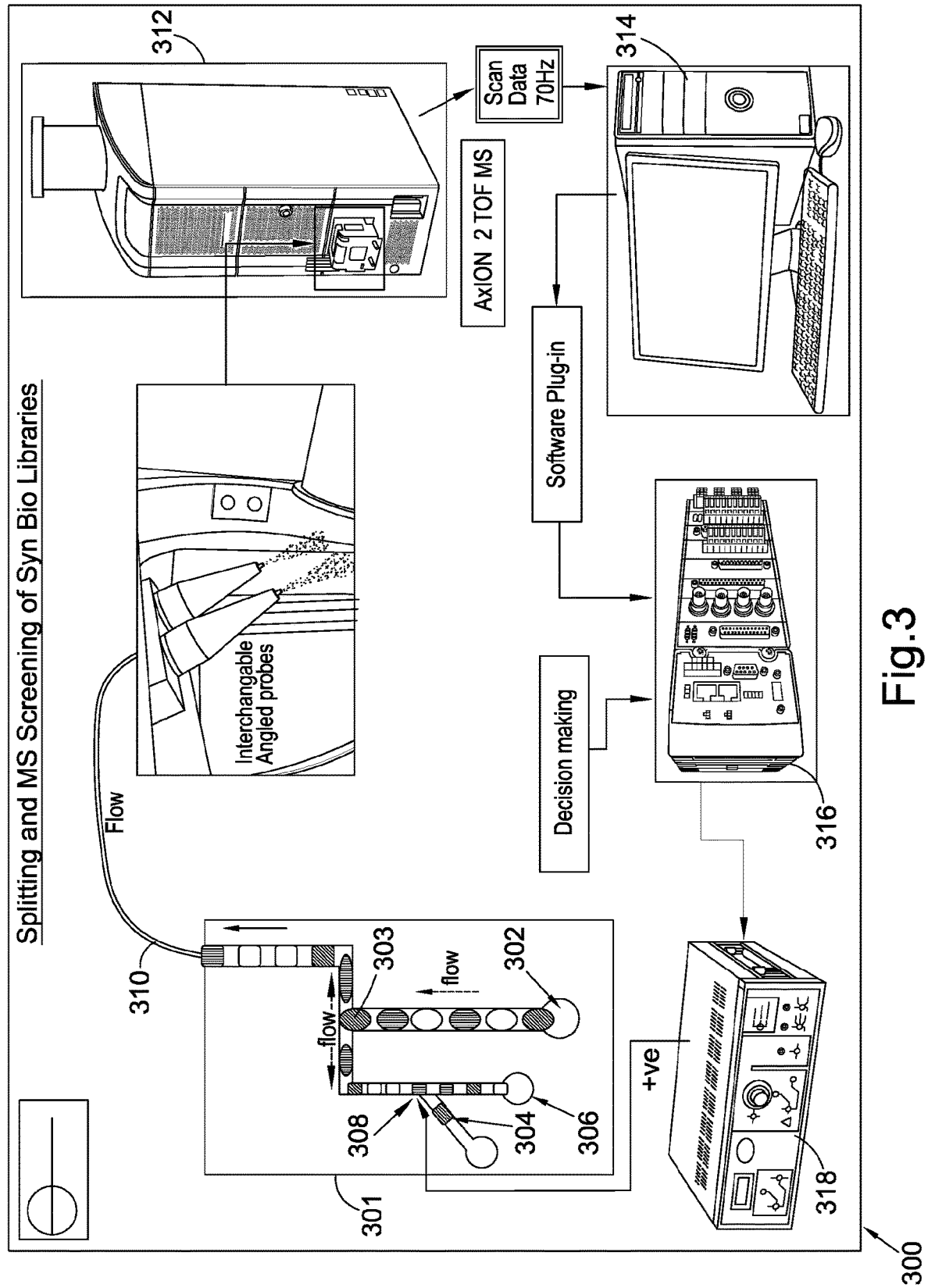
FIG. 3 shows a schematic diagram of a system according to embodiments of the present invention.

FIG. 3 shows a schematic diagram of an embodiment of the system 300 described herein. In this example, a chip 301 is provided which includes, inter alia, a container 302 comprising the parent droplet emulsion, a droplet splitting module 303, and a droplet sorting module 308. Further containers are provided for the sorted second droplets for each of the analysis of the first droplet showing a "hit" (304) and for the analysis of the first droplet showing no "hit" ("waste" container 306).

The microfluidic chip 301, in this example, comprises a connector 310 to connect the channel guiding the first droplet to the emitter of a mass spectrometer unit 312. The constituents of the first droplets are analysed in the mass spectrometer 312, and the resulting data is used as an input for a computer 314 with a processing unit.

Further equipment may be provided to determine whether one or more pre-defined conditions are met when the first droplet is analysed. The computer/processing unit 314 and decision making unit 316 may then be connected to the droplet sorting module 308 which, in this example, is provided on-chip. An amplifier 318 (in this example a HV amplifier 318) may be provided to amplify an output signal by the decision making unit 316 which is provided to the droplet sorting module 308.

Depending on the outcome of the analysis of the first droplet in the mass spectrometer unit 312, i.e. whether a "hit" is determined by the computer/processing unit 314 and the decision making unit 316, the corresponding second droplet is guided to the "waste" container 306 or the "hit" container 304.

As illustrated in FIG. 3 using a colour code for the different droplets to be split, analysed and sorted, a second droplet arrives at the droplet sorting module 308 essentially simultaneously as the corresponding first droplet arrives at the emitter of the mass spectrometer unit 312.

The system and chip design therefore allow a picodroplet, e.g. a water-in-fluorous oil picodroplet, to be (destructively) analysed by, e.g. a mass spectrometer 312, whilst retaining a sample of the second droplet for analysis, such as a genetic analysis. After splitting, the (first) picodroplet to be analysed may hereby be linked to the corresponding (second) picodroplet to be sorted in the droplet sorting module 308.

Figure 4:
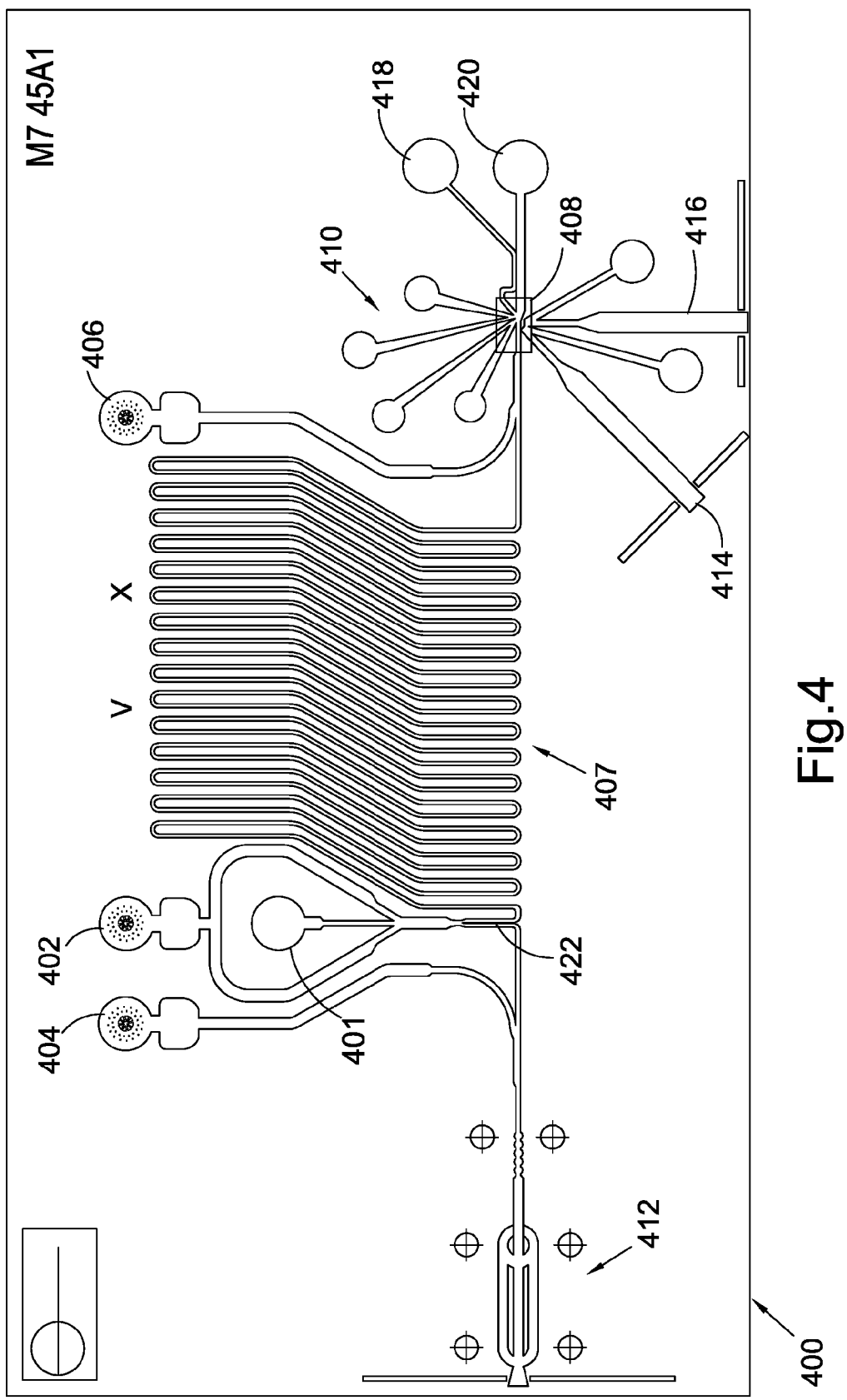
FIG. 4 shows a schematic illustration of a further droplet splitting and sorting chip according to embodiments of the present invention.

FIG. 4 shows a schematic illustration of a further embodiment of the droplet splitting and sorting chip 400 described herein.

In this example, a container 401 which contains the droplets to be split and sorted is provided on the chip 400. Spacing oil 402 is provided in a container on the chip 400 which allows for separating the droplets from container 401 once they are provided to the channel system of the chip 400.

A droplet splitting module 422 is provided to split the droplets from container 401 into pairs of first and second droplets. The first droplet is then provided to a mass spectrometer (not shown in FIG. 4), while the second droplet is further processed as outlined below.

The chip 400 comprises, in this example, a mass spectrometer emitter holder/connection 412 with alignment marks which may be used to connect the chip 400 to the mass spectrometer unit.

In order to separate the first droplets generated in the droplet splitting module 422 which are to be guided to the mass spectrometer, a further spacing oil 404 is provided on the chip 400.

The second droplets generated in the droplet splitting module 422 are, in this example, provided to a delay channel 407 which is arranged between the droplet splitting module 422 and the optical system comprising optical fibres 414, 416. The delay channel may be used to match the time the second droplet needs to reach the optical system with the time the first droplet takes to reach the mass spectrometer unit in which it is analysed. It will be appreciated that the length of the delay channel 407 may be varied to vary the time the second droplet needs to reach the optical system, depending on the length/time the first droplets have to travel to reach the mass spectrometer unit. The delay channel 407, together with the optical system, therefore allows identifying and correlating a second droplet with its (correct) corresponding first droplet which is analysed in the mass spectrometer unit.

In order to separate the second droplets further before they reach the droplet sorting module 408, a further spacing oil 406 is provided in a container on the chip 400.

A first optical fibre 414 and a second optical fibre 416 are provided in this example on the chip 400 and extend to the droplet sorting module 408. The droplets may be analysed or detected optically using the first and second optical fibres 414, 416.

Various electrode channels 410 are in this example provided on the chip 400. Depending on the analysis of the first droplets in the mass spectrometer, the second droplets may be sorted in the droplet sorting module 408 by applying, for example, an electric field to the second droplets.

A second droplet may thereby be sorted in the droplet sorting unit 408 and guided into one of, in this example, two outlets 418, 420.

FIGS. 5*a* and *b* show schematic illustrations and optical images of droplet splitting modules 422, 502 according to embodiments described herein.

In these embodiments, channels in which the first and second droplets, respectively, are guided have different lengths and widths (or width variations). In this example, the channel for the (sibling) droplet 1 is widened earlier in a downstream direction compared to the channel for the (sibling) droplet 2. As a result, the back-pressure in the channel for sibling droplet 1 is lower compared to the back-pressure in the channel for sibling droplet 2. Generally, a droplet preferably flows into the channel with a lower back-pressure. Therefore, in this example, the volume of the sibling droplet 1 is relatively larger compared to the volume of the sibling droplet 2. By varying the geometry of the channels, the respective back-pressures may be varied, which may allow varying the ratio between volumes of the first and second droplets when a droplet is split in the droplet splitting modules 422, 502. This may be particularly preferable as, for example, a viable microorganism which may be contained in a droplet may only survive (at least for a threshold period) if the droplet is not, for example, too small. On the other hand, a droplet may be guided through the microfluidic channels on the chip (or off-chip) at a desired speed only if the size of the droplet is below a threshold. A droplet splitting module 422, 502 as shown in FIGS. 5*a* and *b* may therefore allow for controlling the sizes (i.e. volumes) of the first and second droplets as desired.

It will be appreciated that the original droplet which is to be split may be chosen to be above a threshold size so that the droplet may be split (e.g. split at all), in particular to obtain the desired volumes for the first and second droplets, respectively.

FIG. 6 shows a schematic illustration and an optical image of a droplet sorting unit 408 according to embodiments described herein.

In this example, the droplet sorting unit 408 comprises an incident light guide or channel 602 and a light guide or channel 604 configured to guide the light signal which is to be detected. Electrodes 410 are provided in the droplet sorting unit 408 to guide the second droplet(s) into, in this example, one of a "sorted" channel or outlet and a "waste" channel or outlet (e.g. outlets 418, 420), depending on the analysis of the first droplet(s) in the mass spectrometer.

Figure 7:
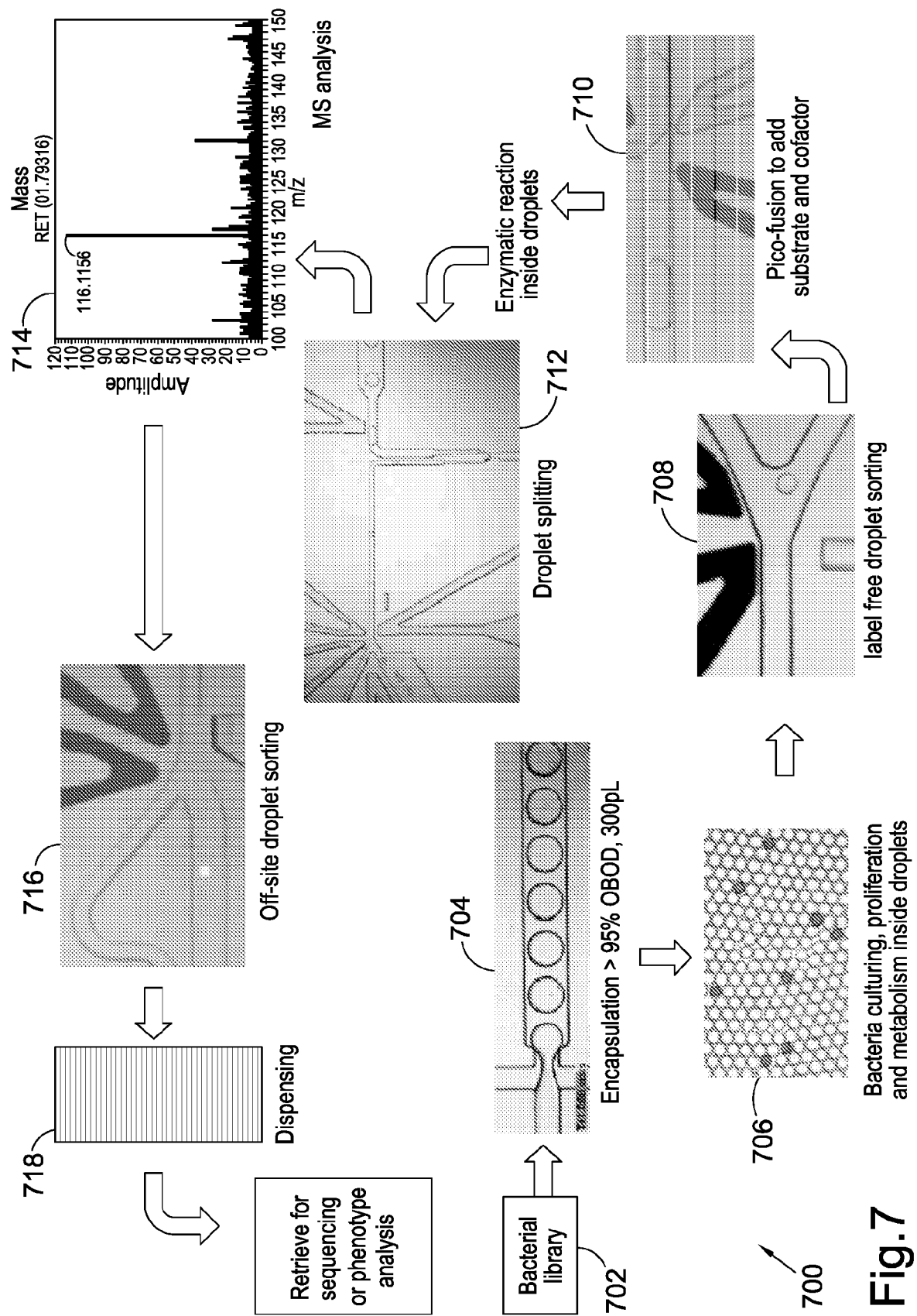
FIG. 7 shows a schematic flow-chart for droplet splitting and sorting using images of data and microfluidic devices generated according to embodiments of the present invention.

FIG. 7 shows a schematic flow-chart 700 for droplet splitting and sorting according to embodiments described herein.

In this example, a bacterial library 702 is to be analysed and sorted, whereby the biological organism is encapsulated in an emulsion. Individual droplets, in this example with a volume of approximately 300 pL are formed at the droplet formation step 704.

A cell culture may be obtained and/or grown, and/or metabolism of the cells may be facilitated inside the droplets at step 706.

The droplets are then, in this example, sorted via label free droplet sorting at step 708. This may for example allow for removing droplets which do not contain a target entity or no entity.

At step 710, pico-fusion may be provided in order to add a substrate to the droplet and/or to add a cofactor, such as, for example, enzymes. An enzymatic reaction inside a droplet may thereby be promoted.

At step 712, a droplet is then split into first and second droplets according to embodiments described herein. The first droplet is then analysed in a mass spectrometer at step 714. The second droplet may then be sorted (in this example off-site/chip) at step 716 dependent on an outcome of the analysis of the first droplet in the mass spectrometer at step 714.

The sorted second droplet may then be dispensed at step 718 and be retrieved for further analysis, for example for sequencing or phenotype analysis, whereby, for example, the constituents (and, in embodiments, their relative amount) of the second droplet are known due to the analysis of the first droplet in the mass spectrometer at step 714.

Figure 8:
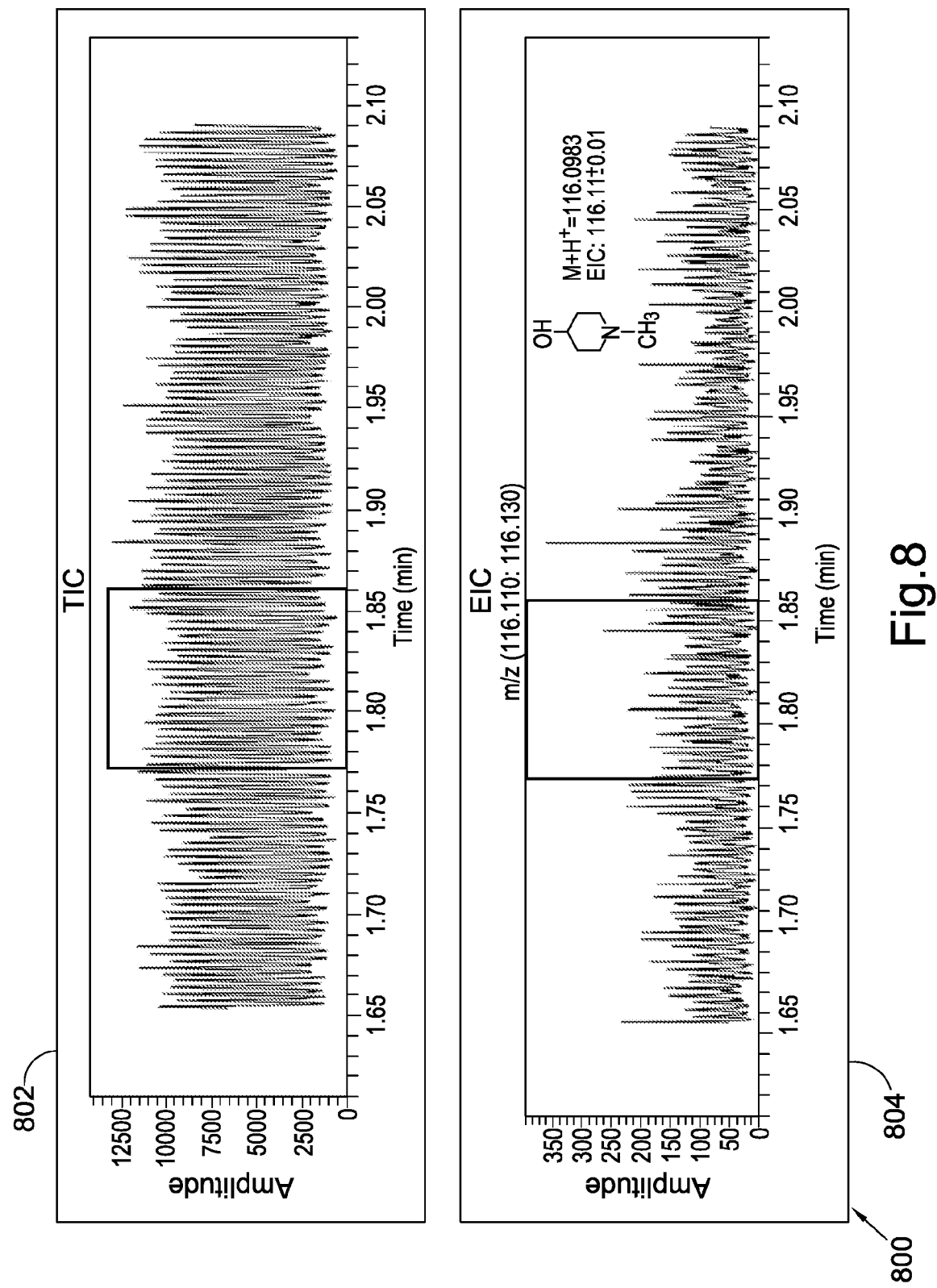
FIG. 8 and FIG. 9 show droplet detection in a mass spectrometer according to embodiments of the present invention.

FIG. 8 shows experimental results of a droplet being detected in a mass spectrometer according to embodiments described herein.

The top part of FIG. 8 shows the total ion current versus time (802), whereas the bottom part of FIG. 8 shows the extracted ion current versus time (804).

Figure 9:
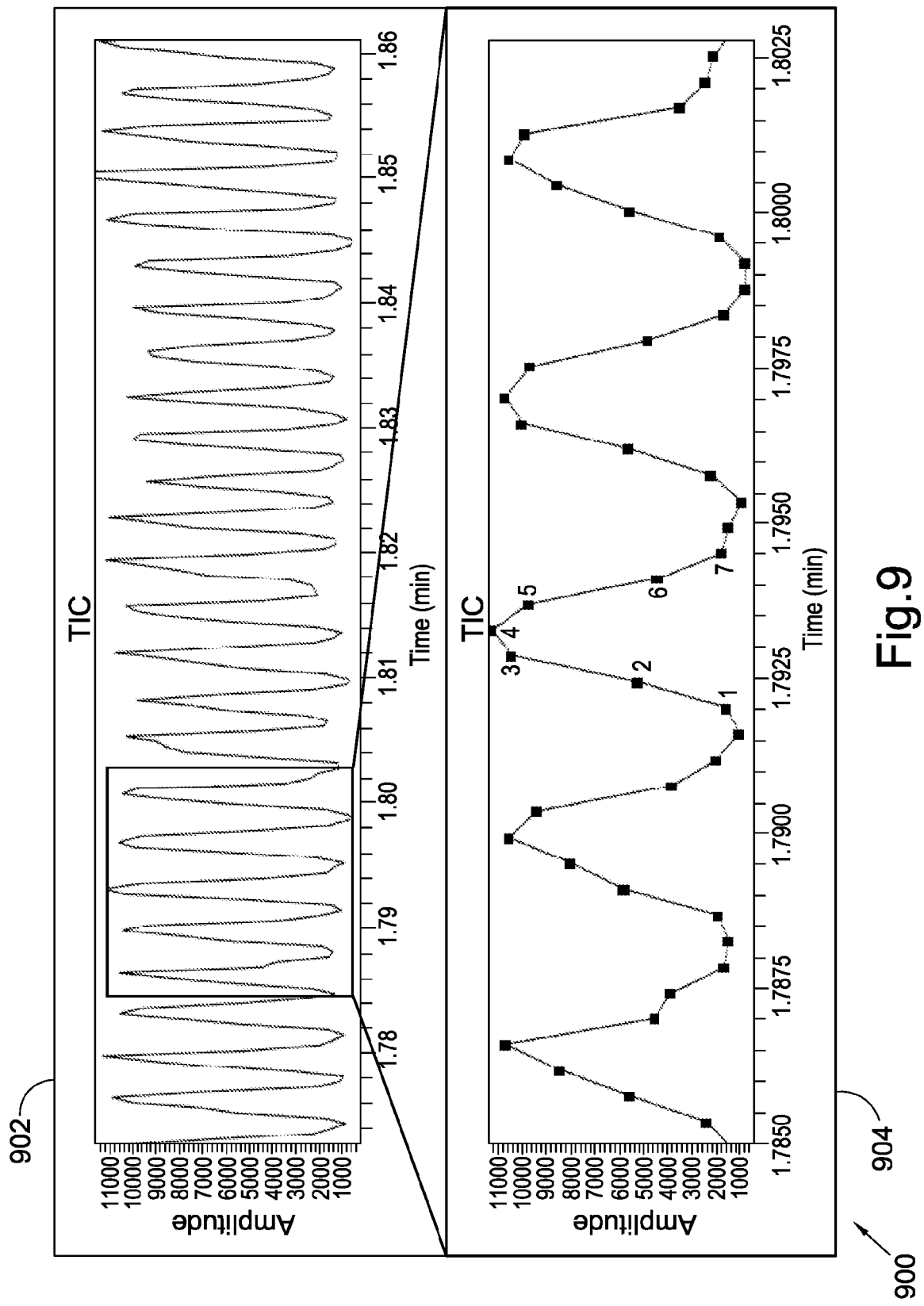

FIG. 9 shows the signal illustrated in 802 of FIG. 8 for a time period of, in this example, approximately 1s. In this example, approximately 5 droplets were detected during a 1s period.

A single droplet may be analysed in the mass spectrometer at various points in time, as shown in the bottom part of FIG. 9. In this example, 7 measurements are taken over a period of approximately 0.2 seconds. The result is shown in FIG. 10.

Figure 10:
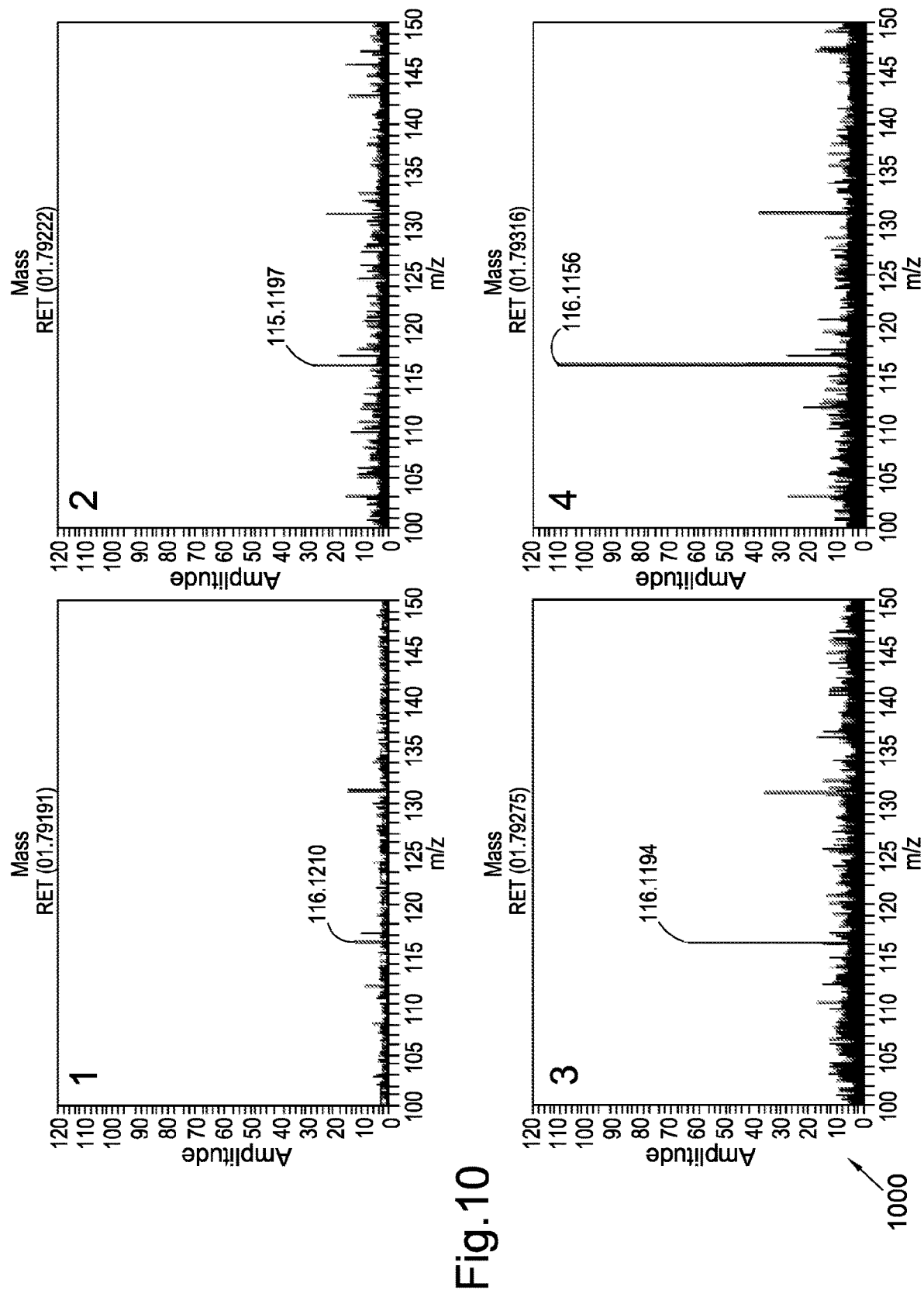
FIG. 10 shows mass spectra across a single droplet according to embodiments of the present invention.
Figure 10:
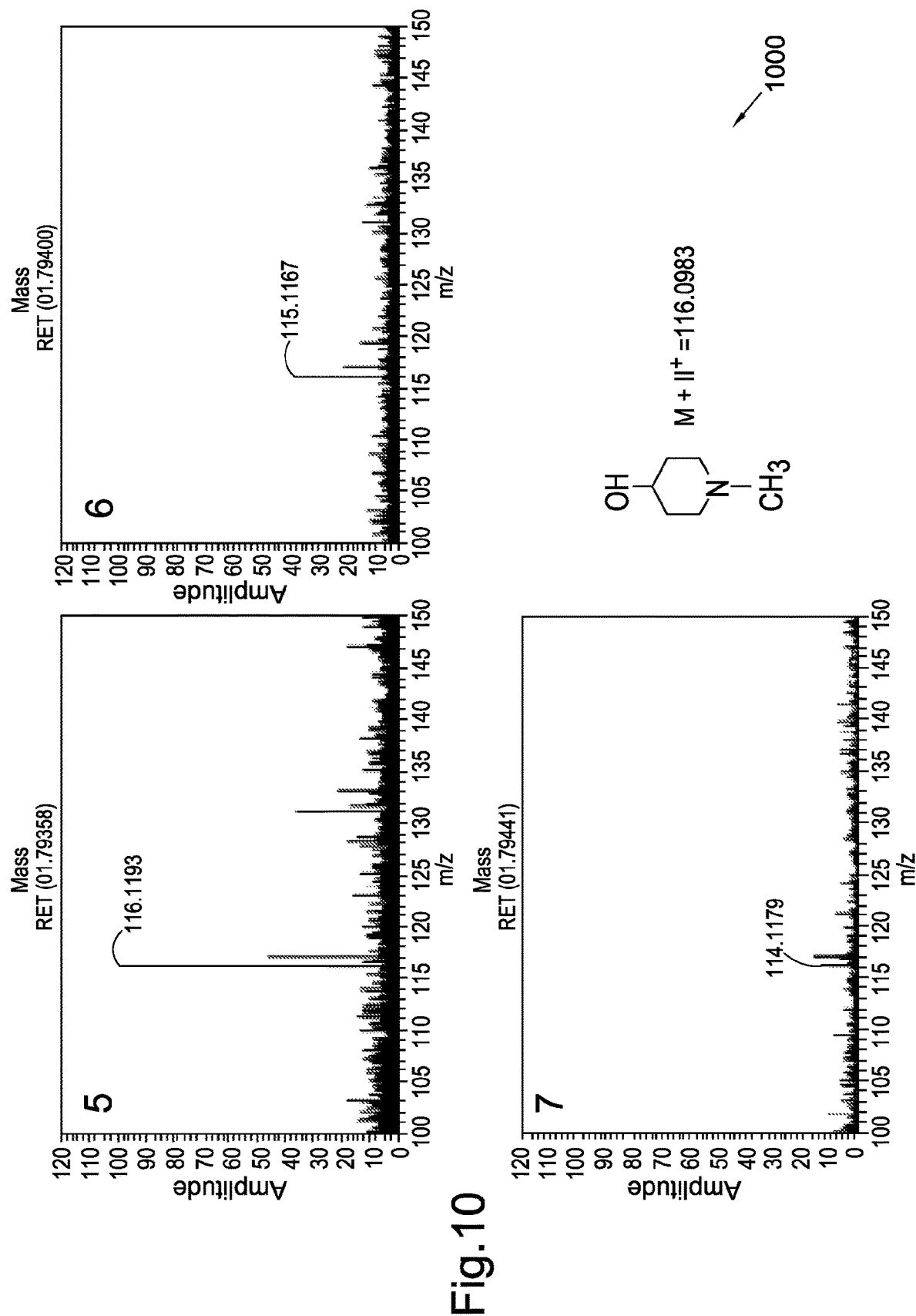

FIG. 10 shows a time series of mass spectrometer measurements 1000 taken at the points in time as indicated in FIG. 9. The time series of FIG. 10 relates to a single droplet which is provided to the mass spectrometer.

As can be seen, the mass spectrometer signal increases until the mass spectrometer 'sees' the full (or a relatively larger part of the) droplet (point 4 in FIGS. 9 and 10). The mass spectrometer signal then increases as the droplet exits the analysing section of the mass spectrometer.

The specific signal, i.e. the specific peaks and their absolute or relative amplitudes may then be analysed to determine the constituents of the droplet. This signal may then be used as described herein with regard to the various embodiments to determine whether a second (sibling) droplet is to be put to waste or sorted according to the analysis of the first droplet in the mass spectrometer.

As outlined above, it may be desirable to sequence the stream of first and second droplets in the path leading to the mass-spectrometer and the optical detection/sorting unit, respectively.

In embodiments, therefore, a population of tag ('coded') droplets may be added to a library of droplets. The tag droplets may contain, for example, a single (or multiple) fluorescent reagents, for example a quantum dot (which may have a diameter of between 1 and 10 nm), a fluorescent bead (which may have a diameter of between 0.01 and 10 um), a fluorescently labelled macromolecule (for example a protein), a fluorescent organic dye, or others.

The tag droplet may further comprise an organic or inorganic molecule (mass tag) which may be correlate to the analytes, biomolecules or metabolites of interest.

The organic or inorganic molecule (mass tag) may have a mass in the mass-to-charge ratio region of the analytes, biomolecules or metabolites of interest and may, preferably be within +/−5000 amu of the analytes, biomolecules or metabolites of interest, preferably within +/−500 amu of the analytes, biomolecules or metabolites of interest and more preferably within +/−50 amu of the analytes, biomolecules or metabolites of interest.

Preferably, the proportion of tag droplets added to the library of droplets comprising the analytes, biomolecules or metabolites of interest is less than 50% of the total combined number of droplets, preferably less than 20% and more preferably less than 10% of the total number of droplets.

The optical system may be arranged such that all the second droplets, including the second tag droplets, may be detected at or near the droplet sorting module/unit using the optical fibres which may be provided on the chip.

The second droplets and second tag droplets may be observed and counted at or near the droplet sorting module using, for example, differential light scattering based detection, using a suitable incident light source. The incident light source may be a light-emitting diode, a laser operating in the wavelength range of, for example, 300-2000 nm, in the visible range region between 300 nm and 750 nm, or in the range 300-500 nm. In embodiments, the wavelength of the light source is approximately 340 nm.

The incident light may be delivered by an optical fibre or may be delivered by a free space optical arrangement in which the detection optical fibre may be at an angle between 0° and 180° to the incident light, and preferably >20° and <90°, more preferably >30° and <60°.

The detector optical fibre may be connected to a suitable dichroic mirror that allows shorter wavelength scattered incident light to be reflected towards a suitable optical detector, for example a photomultiplier tube or an avalanche photodiode, whilst longer wavelength fluorescent light may pass through this first dichroic mirror to another optical detector.

Use of differential light scattering detection of the second droplets may allow for counting the droplets in a label-free manner, which may be especially important for the analysis of droplets containing a single or multiple cells.

Preferably one fluorescent code may be used in the first droplet and the optical arrangement collects light scattered from all second droplets in one optical detector. Fluorescent light may be collected in a second optical detector via one dichroic mirror. To collect light from n different optical codes, n dichroic mirrors and n+1 optical detectors may be used.

The tagged first droplet may contain a single fluorescent nanoparticle, fluorescent bead, fluorescently labelled macromolecule or fluorescent organic dye, but at different set of concentrations may be used along with one or more corresponding mass tags.

Preferably the tag droplet contains a set of concentrations of a single fluorescent nanoparticle, fluorescent bead, fluorescently labelled macromolecule or fluorescent organic dye and an internal calibration molecule so that a specific mass-to-charge ratio for the mass tag to internal calibration standard is particular to each concentration of the fluorescent species used in the droplet.

In a more complex coding/tagging strategy, the first tag droplets may contain either more than one fluorescent nanoparticle, fluorescent bead, fluorescently labelled macromolecule or fluorescent organic dye and may contain one or more mass tags and an appropriate number of internal standards so that the mass-to-charge ratio of the number and concentration of the fluorescent mixture may be decoded by suitable software.

Mass spectral data may be "sipped" from the mass spectrometer and analysed on a computer connected to a digital to analogue converter (DAC) connected to a computer running a suitable analysis software that can rapidly determine the mass-to-charge ratios of all the masses of interest from the first droplets and also collect the optical signals from the second droplets.

First droplets may be analysed in the software and a set of mass-to-charge ratios may be measured for analytes, biomolecules, metabolites as well as for the mass tags used in tag droplets with respect to their internal standards used in both first droplet types by use of a dedicated piece of software.

The software may first count the number of droplets and assign their type based on the observed mass-to-charge ratios detected as either an assay droplet or a barcoded droplet and assigns the droplet a coded number or letter and stores the coded sequence of up to 200 droplets in memory, but preferably a sequence of up to 50 droplets in the memory.

The optical detection system may also be connected to the same hardware and software and counts all the second droplets approaching the sorting module, by measuring the differential light scattered from the droplet and also the fluorescence signals from each second droplet and assigns the second droplet a code, either as a letter or number, this coded sequence of up to 200 second droplets, but preferably up to 50 droplets is stored in a second memory.

The delay line/channel between the droplet splitting module and the droplet sorting module may be designed so that a second droplet takes longer in time to reach the droplet sorting module than the first droplet takes to be analysed, ideally >0.01 seconds but less than 20 seconds, preferably >0.1 seconds but less than 5 seconds and more preferably >0.5 seconds but less than 3 seconds.

The software may also look for droplets from the plurality of droplets with an mass-to-charge ratio greater than a specific threshold set by the user in the software, and are coded as a hit droplet.

The software may compare the two coded droplet sequences of first and second droplets in their respective sets of memory and looks to correctly align the two sequences. Once matched, the software may continue until a mismatch occurs, when the two memory are cleared and the process of sequence alignment may be repeated until the two sequences can be aligned.

When the software is counting and coding the first and second droplets correctly, a hit droplet can be selectively sorted after the appropriate delay for it to arrive at the droplet sorting module, where an appropriate electrical signal is sent from the DAC to a high voltage amplifier to allow the droplet to be moved in to a sorting channel by use of, for example, a dielectrophoretic force.

Droplets collected from the sorting channel may then be stored either in a temperature controlled vessel or may be dispensed by a suitable apparatus into, for example, a microtitre plate.

The software may store information about each hit first droplet and the position of the second droplet in the microtitre plate.

Figure 11A:
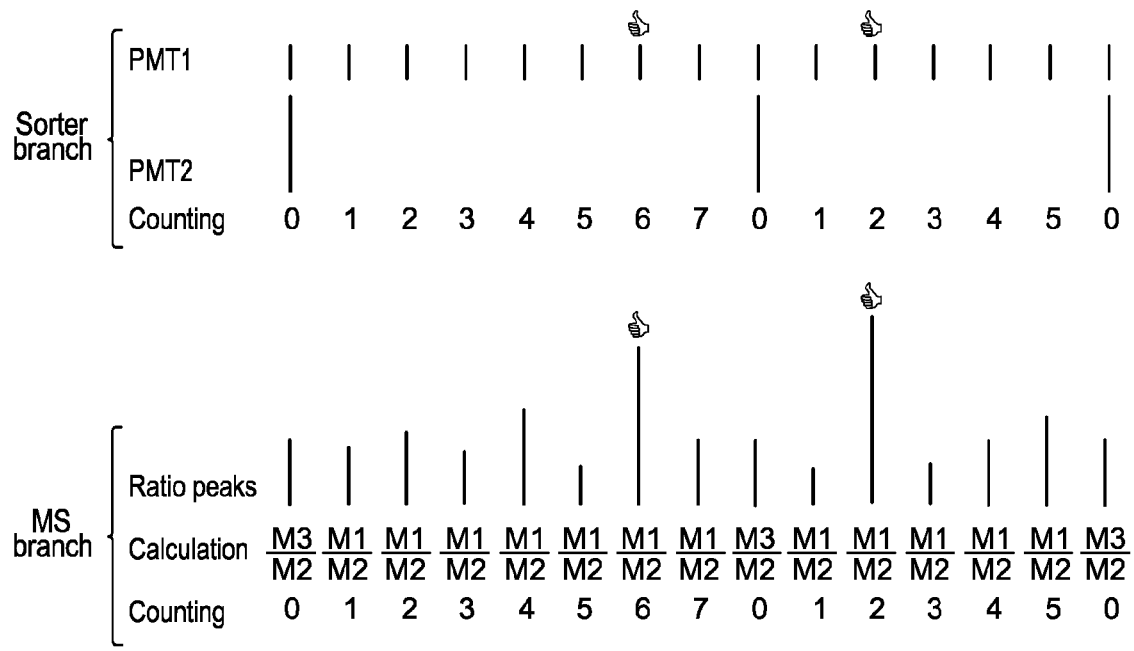
FIG. 11a and FIG. 11b illustrate the operation of example embodiments of a sibling droplet alignment procedure.
Figure 11B:
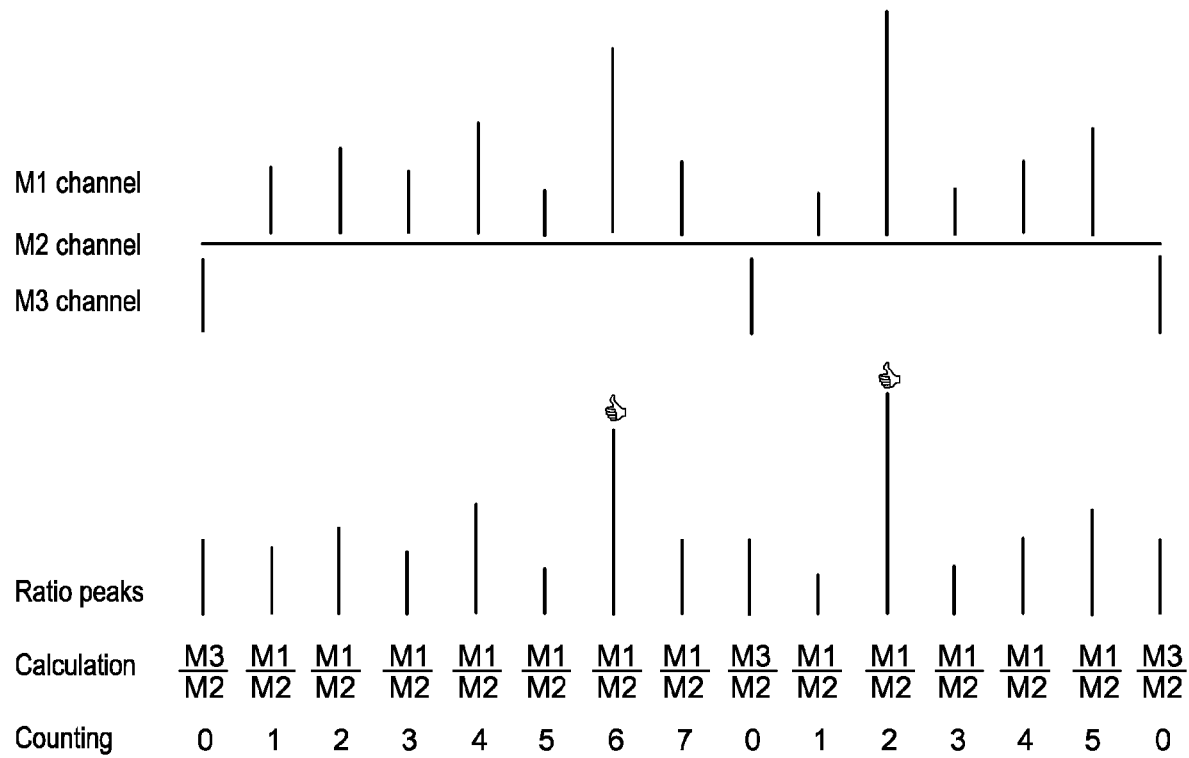

FIGS. 11a and 11b illustrate the operation of example embodiments of a sibling droplet alignment procedure of the type we have previously described. The "sorter" branch is the optical branch. PMT labels photomultipliers where PMT1 detects scattered light and PMT2 detects a tag. The MS branch is the mass spectrometer branch. As illustrated, in practice rather than work with an m/z value (such as M1, M2 or M3) directly, instead ratios of M1 (target material) and M3 (tag material) to a reference molecule m/z (M2) are used, where the reference material may be within a droplet or provided separately to the mass spectrometer.

Embodiments of the method and system described herein may be exploited in a variety of fields. In particular, embodiments allow for a label-free sorting and/or analysis of synthetic biology libraries for, e.g. metabolic process optimisation, for libraries designed for protein evolution, and/or for finding cells or transcripts that produce novel or high yields of (a) specific molecule(s). Droplet contents may be, for example, extracted, say for analysis and/or replication of the contents, or processed in some other way, for example analysed in situ. In addition, although in embodiments we have described example applications in which droplets are held in a liquid, in other approaches the droplets may be disposed in a gas. For the avoidance of doubt, where a fluid is referred to this may be either a liquid or a gas, although in preferred embodiments the fluid is a liquid, in particular an oil such as a flourous oil; and preferably the droplet is an aqueous droplet (and in practice droplets may be of a variety of different shapes)

It will be understood that these are only examples of possible implementations of the embodiments described herein. The skilled person will appreciate that embodiments may be used in many alternative areas.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method in a microfluidics device comprising:
   providing a target droplet comprising a plurality of constituents,
   providing a tag droplet in an emulsion comprising the target droplet and tag droplet, said tag droplet comprising a first tag and a second tag,
   splitting said target droplet in the emulsion into a first target droplet and a second target droplet, wherein said first target droplet comprises a first fraction of said plurality of constituents and said second target droplet comprises a second fraction of said plurality of constituents, wherein said first target droplet and said second target droplet comprise the same constituents,
   splitting said tag droplet in the emulsion into a first tag droplet and a second tag droplet, wherein said first tag droplet comprises the first tag and said second tag droplet comprises the second tag,
   providing said first target droplet and said first tag droplet into a first stream of droplets, and providing said second target droplet and said second tag droplet into a second stream of droplets,
   detecting said first tag droplet and detecting said second tag droplet,
   ionizing said constituents of said first fraction of said plurality of constituents in said first target droplet,
   measuring a mass-to-charge ratio of said ionized constituents,
   correlating said second target droplet with said first target droplet to enable identification of the second target droplet using said first tag droplet and said second tag droplet,
   determining the constituents of said second target droplet from said measuring of said constituents of said first target droplet, and
   sorting said second target droplet dependent on an outcome of said measuring.

2. A method as claimed in claim 1, wherein said second target droplet is sorted if said measured mass-to-charge ratio of a said ionised constituent coincides with a pre-defined mass-to-charge ratio or with one of a plurality of pre-defined mass-to-charge ratios.

3. A method as claimed in claim 2, wherein said pre-defined mass-to-charge ratio or plurality of pre-defined mass-to-charge ratios comprise a range or plurality of ranges of mass-to-charge ratios, respectively.

4. A method as claimed in claim 1, wherein said measuring comprises measuring an intensity of said measured mass-to-charge ratio of said ionised constituents above or below a pre-defined threshold intensity and/or measuring a pre-defined signal mass spectrometer pattern change across a plurality of said ionised constituents.

5. A method as claimed in claim 1, wherein said ionising comprises electrospray ionising said constituents of said first fraction of said plurality of constituents in said first target droplet.

6. A method as claimed in claim 1, wherein said analysing comprises analysing said constituents of said first fraction of said plurality of constituents in said first droplet in a first region, and wherein said sorting comprises sorting said second droplet in a second region remote from said first region.

7. A method as claimed in claim 1, wherein said sorting comprises dielectrophoretic sorting said second droplet.

8. A method as claimed in claim 1, wherein providing said droplet comprises providing a plurality of droplets,
   wherein a said droplet of said plurality of droplets is separated from a neighbouring said droplet of said plurality of droplets by a first spacing fluid,
   wherein a said first droplet is separated from a neighbouring said first droplet by a second spacing fluid, and
   wherein a said second droplet is separated from a neighbouring said second droplet by a third spacing fluid.

9. A method as claimed in claim 8, wherein said first, second and third spacing fluids comprise first, second and third oils, or first, second and third water-in-oil emulsions.

10. A method as claimed in claim 1, wherein said analysing and said sorting are performed in tandem or with a known time delay.

11. A method as claimed in claim 1, wherein said sorting said second droplet is dependent exclusively on an outcome of said measuring.

12. A system comprising:
   a droplet splitting module adapted to split a target droplet into a first target droplet and a second target droplet, wherein said target droplet comprises a plurality of constituents, and wherein said first target droplet comprises a first fraction of said plurality of constituents and said second target droplet comprises a second fraction of said plurality of constituents, and wherein said first target droplet and said second target droplet comprise the same constituents, wherein the droplet splitting module is further adapted to split a tag droplet into a first tag droplet and a second tag droplet, wherein said first tag droplet comprises a first tag and said second tag droplet comprises a second tag, fluidic channels arranged to provide said first target droplet and said first tag droplet into a first stream of droplets, and providing said second target droplet and said second tag droplet into a second stream of droplets, a first detector for detecting said first tag droplet, an analyser adapted to ionize said constituents of said first fraction of said plurality of constituents in said first target droplet and measure a mass-to-charge ratio of said ionized constituents, a droplet sorting module configured to sort said second target droplet, and a feedback system in communication with said analyser and said droplet sorting module, wherein said feedback system is configured to correlate said second target droplet with said first target droplet and confirm that correct first and second target droplets are correlated based at least on a signal detected from the first tag droplet, determine the constituents of said second target droplet from said measurement of said constituents of said first target droplet, and control said sorting of said second target droplet in said droplet sorting module dependent on an outcome of said measurement of said constituents of said first fraction of said plurality of constituents in said first target droplet in said analyser.

13. A system as claimed in claim 12, wherein said analyser comprises an electrospray ionisation mass spectrometer configured to ionise said constituents of said first fraction of said plurality of constituents in said first target droplet and measure a mass-to-charge ratio of said ionised constituents.

14. A system as claimed in claim 13, wherein said droplet sorting module sorts said second target droplet if said measured mass-to-charge ratio of a said ionised constituent coincides with a pre-defined mass-to-charge ratio or with one of a plurality of pre-defined mass-to-charge ratios.

15. A system as claimed in claim 14, wherein said pre-defined mass-to-charge ratio or plurality of pre-defined mass-to-charge ratios comprise a range or plurality of ranges of mass-to-charge ratios, respectively.

16. A system as claimed in claim 13, wherein said measuring comprises measuring an intensity of said measured mass-to-charge ratio of said ionised constituents above or below a pre-defined threshold intensity and/or measuring a pre-defined signal mass spectrometer pattern change across a plurality of said ionised constituents.

17. A system as claimed in claim 12, wherein said droplet sorting module is configured to sort said second droplet using dielectrophoresis.

18. A system as claimed in claim 12, the system further comprising:
a first spacing fluid to separate a said droplet from a neighbouring said droplet,
a second spacing fluid to separate a said first droplet from a neighbouring said first droplet, and
a third spacing fluid to separate a said second droplet from a neighbouring said second droplet, wherein said first, second and third spacing fluids comprise first, second and third oils, or first, second and third water-in-oil emulsions.

19. A system as claimed in claim 12, wherein said feedback system is further configured to initiate said sorting of said second droplet in said droplet sorting module in tandem with said analysis of said constituents of said first fraction of said plurality of constituents in said first droplet in said analyser, and/or
wherein the system further comprises a delay line such that said second droplet is sorted in said droplet sorting module in tandem with said analysis of said constituents of said first fraction of said plurality of constituents in said first droplet.

20. A microfluidic chip comprising:
a droplet splitting module configured to split a target droplet in an emulsion with a tag droplet into a first target droplet and a second target droplet, wherein said target droplet comprises a plurality of constituents, and wherein said first target droplet comprises a first fraction of said plurality of constituents and said second target droplet comprises a second fraction of said plurality of constituents, and configured to split said tag droplet into a first tag droplet and a second tag droplet, wherein said first tag droplet comprises a first tag and said second tag droplet comprises a second tag, an analyser configured to ionize said constituents of said first fraction of said plurality of constituents in said first target droplet and to measure a mass-to-charge ratio of said ionized constituents, a detector arranged to detect said first tag droplet, a first channel connecting said droplet splitting module and said analyser for guiding a said first target droplet from said droplet splitting module to said analyser;

a droplet sorting module for sorting said second target droplet, a second channel connecting said droplet splitting module and said droplet sorting module for guiding a said second target droplet from said droplet splitting module to said droplet sorting module;

a feedback system in communication with said analyser and said droplet sorting module, wherein said feedback system is configured to correlate said second target droplet with said first target droplet to enable identification of the second target droplet using said first tag droplet and said second tag droplet, determine the constituents of said second target droplet from said measurement of said ionized constituents of said first target droplet, and control said sorting of said second target droplet in said droplet sorting module dependent on an outcome of said measurement of said constituents of said first fraction of said plurality of constituents in said first target droplet in said analyser; and a connector connecting said droplet sorting module and said feedback system.

* * * * *